United States Patent
Xu

(10) Patent No.: US 11,976,081 B2
(45) Date of Patent: May 7, 2024

(54) INTERMEDIATE OF ERIBULIN AND SYNTHESIS METHOD AND USE THEREOF

(71) Applicant: BEIJING TIENYI LUFU PHARMATECH CO. LTD, Beijing (CN)

(72) Inventor: Weiping Xu, Beijing (CN)

(73) Assignee: BEIJING TIENYI LUFU PHARMATECH CO. LTD., Beijing (CN)

( * ) Notice: Subject to any disclaimer, the term of this patent is extended or adjusted under 35 U.S.C. 154(b) by 136 days.

(21) Appl. No.: 17/594,693

(22) PCT Filed: Apr. 2, 2020

(86) PCT No.: PCT/CN2020/082933
§ 371 (c)(1),
(2) Date: Oct. 26, 2021

(87) PCT Pub. No.: WO2020/216034
PCT Pub. Date: Oct. 29, 2020

(65) Prior Publication Data
US 2022/0204523 A1    Jun. 30, 2022

(30) Foreign Application Priority Data
Apr. 26, 2019 (CN) .......................... 201910346140.7

(51) Int. Cl.
| | | |
|---|---|---|
| *C07C 43/23* | (2006.01) | |
| *C07D 303/04* | (2006.01) | |
| *C07D 317/22* | (2006.01) | |
| *C07D 493/22* | (2006.01) | |

(52) U.S. Cl.
CPC ............ *C07D 493/22* (2013.01); *C07C 43/23* (2013.01); *C07D 303/04* (2013.01); *C07D 317/22* (2013.01)

(58) Field of Classification Search
None
See application file for complete search history.

(56) References Cited

FOREIGN PATENT DOCUMENTS

| CN | 103237780 A | 8/2013 |
|---|---|---|
| CN | 105524064 A | 4/2016 |
| CN | 106946906 A | 7/2017 |

OTHER PUBLICATIONS

Srinivas. Theegala et al. "Total Synthesis of Catenioblin B", Tetrahedron Letters, vol. 55, No. 43, Sep. 16, 2014, ISSN: 0040-4039, p. 5953, scheme 2.
Goto, Tomomi et al. "Total Synthesis of Four Stereoisomers of (4Z, 7Z, IOZ, 12E, 16Z, 18E)-14, 20-Dihydroxy-4, 7, 10, 12, 16, 18-Docosahexaenoic Acid and Their Anti-inflammatory Activities", The Journal of Organic Chemistry, vol. 80, No. 15, Jul. 14 2015, ISSN: 0022-3263, p. 7715, scheme 3.
Orita, Akihiro et al. "Integration of Solventless Reaction in a Multi-Step Process:Application to an Efficient Synthesis of PA-824", Advanced Synthesis & Catalysis, vol. 349, No. 13, Sep. 6, 2007, ISSN: 1615-4169, p. 2137, table 1.
Murga. Juan et al. "Stereoselective Synthesis of Microcarpalide", Organic Letters, vol. 4, No. 20, Aug. 30, 2002, ISSN: 1523-7060, p. 3448, scheme 2.
Zheng, Wanjun et al. "Macrocyclic Ketone Analogues of Halichondrin B", Bioorganic & Medicinal Chemistry Letters, vol. 14, No. 22, Sep. 21, 2004, ISSN: 0960-894X, p. 5551-5554.

*Primary Examiner* — Samantha L Shterengarts
(74) *Attorney, Agent, or Firm* — NKL Law; Allen Xue

(57) ABSTRACT

An intermediate compound is prepared and used for the synthesis of halichondrin B, eribulin or an analog thereof, particularly a structural fragment C27-C35 thereof. The starting materials of the synthetic route are readily available, and the optical purity of the starting materials can be ensured, so that the optical purity of the structural fragment C27-C35 in halichondrin B, eribulin or the analog thereof is ensured. Steps for constructing a chiral center of the structural fragment C27-C35 feature higher diastereoselectivity and yield, in particular preparation methods of compounds of formulae (X), (XI), (XVI) and (XV). By-products of partial reactions can be removed only by recrystallization, which results in easy purification and significant reduce in cost.

9 Claims, 2 Drawing Sheets

1 Detector A Ch1/220 nm

Table for peaks

Detector A Ch1 220 nm

| Peak# | Retention time | Area | Height | Area% | Height% |
|---|---|---|---|---|---|
| 1 | 12.466 | 3325384 | 187031 | 99.861 | 99.910 |
| 2 | 22.639 | 4645 | 169 | 0.139 | 0.090 |
| Total | | 3330029 | 187200 | 100.000 | 100.000 |

INTERMEDIATE OF ERIBULIN AND SYNTHESIS METHOD AND USE THEREOF

CROSS-REFERENCE TO RELATED APPLICATIONS

The present application is a U.S. national entry of PCT international application no. PCT/CN2020/082933, filed Apr. 2, 2020, which claims priority to Chinese Patent No. 2019103461407 filed to China National Intellectual Property Administration on Apr. 26, 2019 and entitled "INTERMEDIATE OF ERIBULIN AND SYNTHESIS METHOD AND USE THEREOF", which is incorporated herein by reference in its entirety.

TECHNICAL FIELD

The present invention relates to the field of drug synthesis, and particularly relates to an intermediate of eribulin and a synthesis method and use thereof.

BACKGROUND

Halichondrin B is a structurally complex natural product in cavernosum, and it has strong anti-tumor effect and wide druggability prospect. However, the development progress has been limited due to the limited supply of halichondrin B from natural sources.

Eribulin is a macrocyclic ketone analog obtained by structural optimization of halichondrin B. Eribulin mesylate injection has been approved by the FDA in the United States for the treatment of metastatic breast cancer.

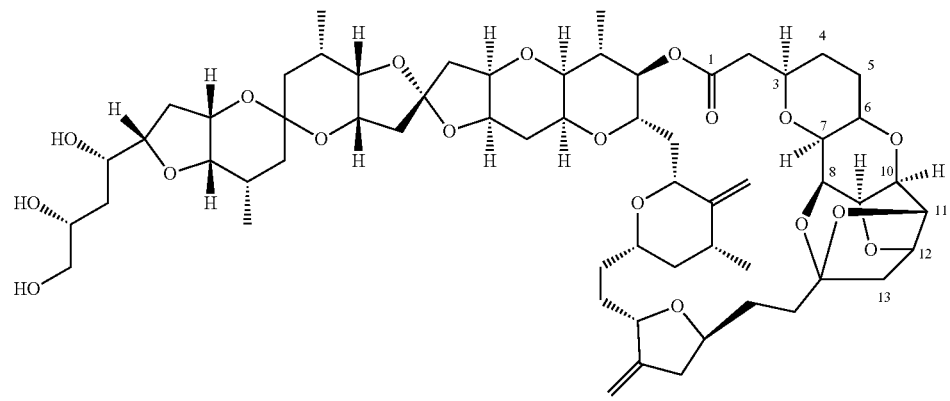

Halichondrin B

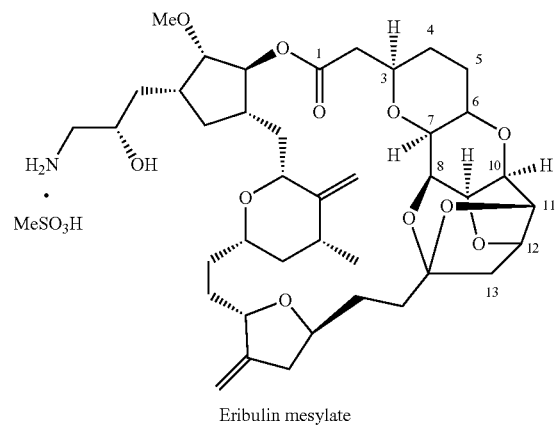

Eribulin mesylate

Eribulin is structurally complex as it contains 19 chiral carbon atoms in the molecule. The total synthesis route used at present has up to 62 steps, and the stereo-control in the total synthesis process is a technical challenge, which is even called as "Mount Everest" of the chemical drug synthesis by industry insiders.

The existing synthetic methods of eribulin or analogues thereof have a plurality of defects. For example, the synthetic route is too lengthy, the optical purity of the starting material is difficult to control, and the purification of intermediates is complicated and costly. In addition, some reactions used in the synthesis methods described above are poor in stereoselectivity, and isomers with similar properties are easily to be formed and difficult to be removed in the synthesis process due to the presence of numerous chiral carbon atoms in the product molecules, and thus the purity of the product cannot be ensured.

Therefore, it is highly desirable to develop a method for synthesizing intermediates of eribulin or its analogs that can improve the synthesis efficiency, facilitate the stereoselectivity, and simplify the purification operation.

SUMMARY

In order to solve the above problems, the present invention provides a compound of the following formula (IX):

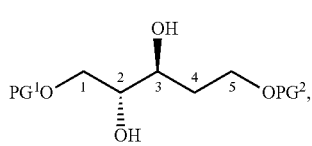

wherein, $PG^1$ and $PG^2$ are the same or different and are each independently selected from hydroxyl protecting groups; a chiral center absolute configuration of the compound is (2R, 3S).

According to an embodiment of the present invention, the hydroxyl protecting group is selected from substituted or unsubstituted alkyl, alkenyl, cycloalkyl, aryl, heteroaryl, heterocyclyl, acyl, sulfonyl, alkyloxycarbonyl, arylalkyloxycarbonyl, groups obtained by removing OH groups from inorganic acids, phosphinothioyl and silyl.

According to an embodiment of the present invention, $PG^1$ and $PG^2$ are the same or different, and are each independently selected from substituted or unsubstituted alkyl, alkenyl, cycloalkyl, aryl, heteroaryl, heterocyclyl and silyl; as an example, they may be selected from methoxybenzyl (PMB), benzyl (Bn), triphenylmethyl (Tr), trimethylsilyl (TMS), tert-butyldiphenylsilyl (TBDPS) and tert-butyldimethylsilyl (TBS).

The present invention also provides a preparation method of the compound of formula (IX), which comprises: with D-2-deoxyribose (I) as a starting material, carrying out multi-step reactions including oxidation, hydroxyl protection, reduction ring opening, hydroxyl protection removal and the like to give the compound of formula (IX).

According to an embodiment of the present invention, with D-2-deoxyribose (I) as the starting material, the compound of formula (IX) can be prepared by the following route:

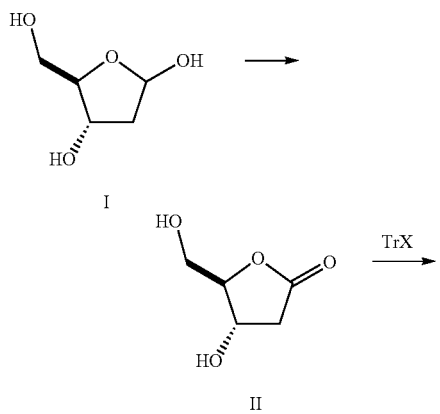

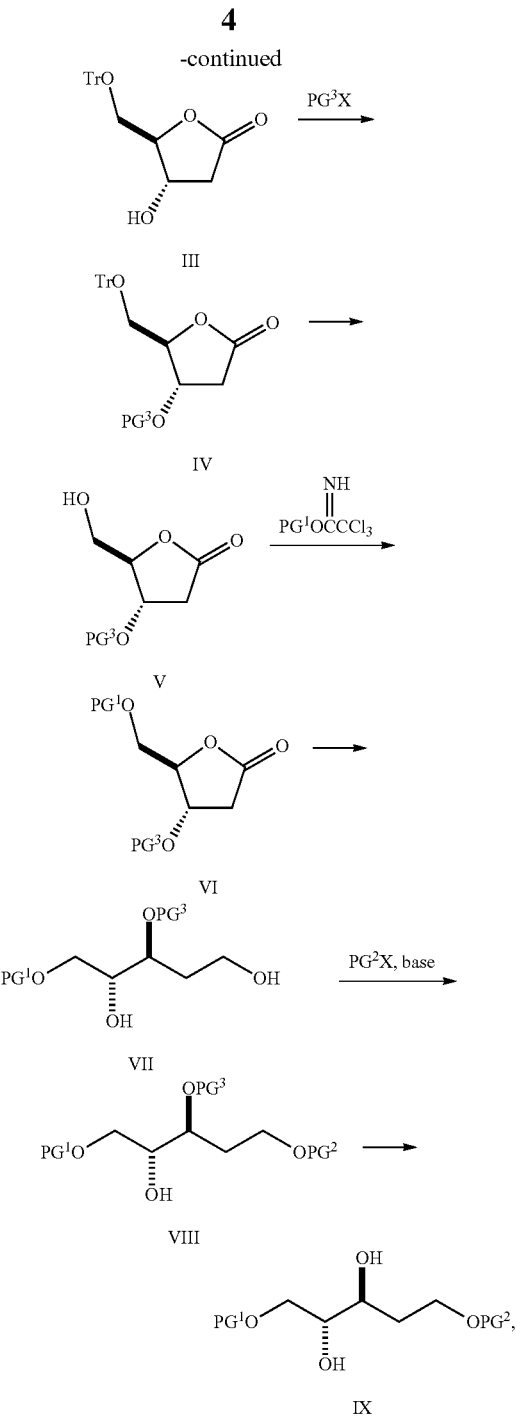

wherein, $PG^1$ and $PG^2$ are defined as above; $PG^3$ is independently selected from the hydroxyl protecting groups described above; all the X are the same or different and are independently selected from halogen. preferably, the compound of formula (II) is obtained by subjecting the compound of formula (I) to liquid bromine oxidation reaction; the compound of formula (III) is obtained by the substitution reaction of the compound of formula (II) and TrX in the presence of DMAP and pyridine; the compound of formula (IV) is obtained by the reaction of the compound of formula (III) and $PG_3X$ in the presence of DMAP and imidazole; the compound of formula (V) is obtained by removing Tr from the compound of formula (IV) at low temperature in the presence of BX$_3$; the compound of formula (VI) is obtained by reacting the compound of formula (V) with

the compound of formula (VII) is obtained by reduction ring opening of the compound of formula (VI) in the presence of borane dimethyl sulfide; the compound of formula (VIII) is obtained by reacting the compound of formula (VII) with PG$_2$X in the presence of a catalyst

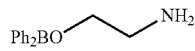

as well as a base and potassium iodide; the compound of formula (IX) is obtained by removing PG$_3$ from the compound of formula (VIII) in the presence of TBAF; wherein PG$_1$, PG$_2$, PG$_3$ and X are defined as above.

According to an embodiment of the present invention, the base may be selected from organic bases and inorganic bases, for example, from one, two or more of the following: sodium carbonate, potassium carbonate, cesium carbonate, sodium bicarbonate, potassium bicarbonate, sodium hydroxide, potassium hydroxide, lithium hydroxide, alkyl lithium, sodium methoxide, sodium ethoxide, methylamine, ethylamine, propylamine, isopropylamine, dimethylamine, diethylamine, diisopropylamine and triethylamine; X may be selected from fluorine, chlorine, bromine and iodine, such as chlorine or bromine. In view of the low price and the 100% optical purity of commercially available D-2-deoxyribose (I), the optical purity of the compound of formula (IX) according to an embodiment of the present invention can be 99.9% or more.

The present invention also provides a preparation method of a compound of formula (X) shown below with the compound of formula (IX) as a starting material, comprising:

(1) reacting the compound of formula (IX) with

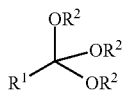

to give a compound of formula (IXa);

(2) reacting the compound of formula (IXa) with an acid halide

or a halosilane R$^3{}_3$SiX to give a compound of formula (IXb-1) and/or a compound of formula (IXb-2); and (3) subjecting the compound of formula (IXb-1) and/or the compound of formula (IXb-2) to alcoholysis under basic conditions and further intramolecular S$_N$2 ring closing reaction to give the compound of formula (X);

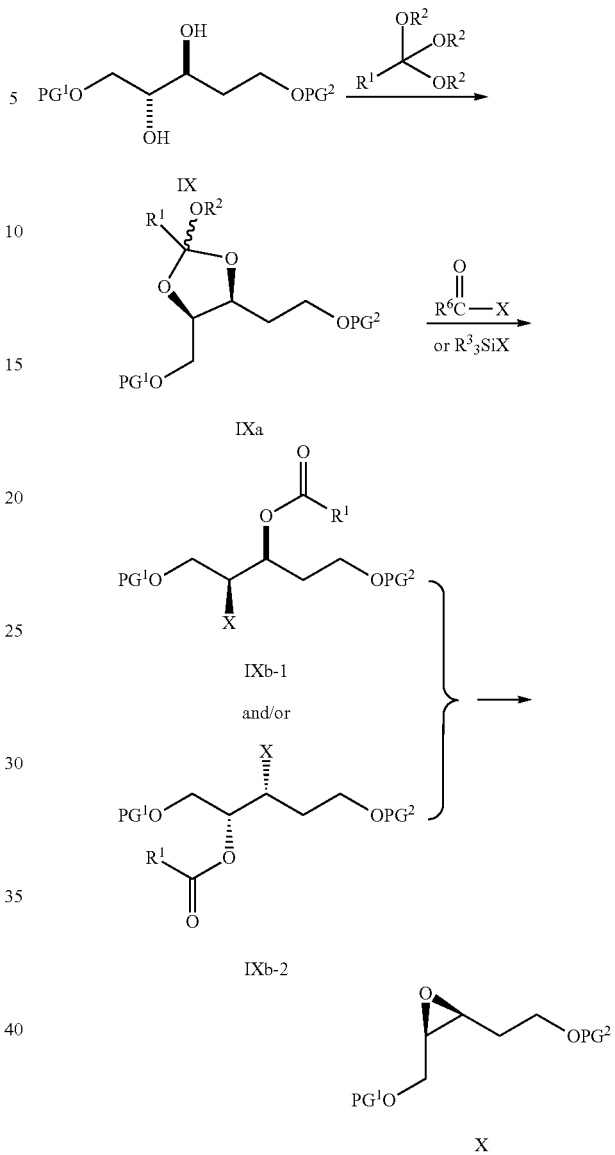

wherein PG$^1$, PG$^2$ and all the X are independently defined as above; R$^1$, R$^2$ and R$^3$ are the same or different and are each independently selected from H, alkyl and aryl; R$^6$ is selected from alkyl. According to an embodiment of the present invention:

in the step (1), the reaction may be carried out in the presence of a catalyst, preferably an acidic catalyst. The acidic catalyst is selected from acidic catalysts suitable for transesterification, for example, from one, two or more of pyridinium p-toluenesulfonatenates (PPTs) and protic acids (e.g., sulfuric acid, phosphoric acid or hydrogen chloride);

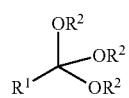

may be selected from orthoester compounds, such as any one of trimethyl orthoformate, triethyl orthoformate, trimethyl orthoacetate, triethyl orthoacetate, trimethyl orthobenzoate and triethyl orthobenzoate;

the temperature of the reaction may be 10-40° C., such as 20-30° C.; the time of the reaction may be 0.5-2 h, such as 1 h;

the molar ratio of the compound of formula (IX) to

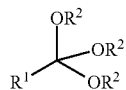

may be 1:(1-5), such as 1:(1-3), such as 1:(1.2-1.8), such as 1:1.5; when a catalyst is present, the molar ratio of compound of formula (IX) to the catalyst may be 1:(0.01-0.2), such as 1:(0.01-0.1), such as 1:0.05;

in the step (2), the temperature of the reaction may be 10-40° C., such as 20-30° C.; the time of the reaction may be 0.1-2 h, such as 0.5 h;

the molar ratio of the compound of formula (IXa) to the acid halide

or halosilane $R^3SiX$ may be 1:(1-5), such as 1:(1-3), such as 1:(1.2-1.8), such as 1:1.5;

in the step (3), the reaction may be carried out in the presence of a base; the temperature of the reaction may be 10-40° C., such as 20-30° C.; the time of the reaction may be 5-15 h, such as 8-12 h;

the molar ratio of the compound of formula (IXb-1) and/or the compound of formula (IXb-2) to the base may be 1:(1-10), such as 1:(1-5), such as 1:(1.5-2.5), such as 1:2.

According to an embodiment of the present invention, the step (3) is carried out in a solvent, such as an alcoholic solvent (e.g., methanol, ethanol, isopropanol or ethylene glycol), water, or a mixture thereof; for example, the weight-volume ratio of the compound of formula (IX) to the solvent is 1 g:(1-20) mL, such as 1 g:10 mL.

The above preparation method ensures that the absolute configuration of both chiral centers remains unchanged during the conversion of the compound of formula (IX) to the compound of formula (X), thereby ensuring a correlation between the optical purity of the compound of formula (X) and the optical purity of the compound of formula (IX), i.e., the compound of formula (X) obtained from the high-purity compound of formula (IX) is also of corresponding high purity.

The present invention also provides a compound of formula (XI) shown below:

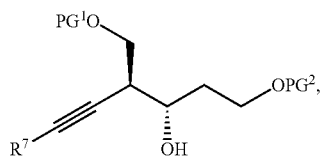

wherein $PG^1$ and $PG^2$ are defined as above; $R^7$ is hydrogen or a terminal alkyne protecting group. The protecting group may be selected from silyl, such as trialkylsilyl (e.g., trimethylsilyl, triethylsilyl or triisopropylsilyl), tert-butyldiphenylsilyl, tert-butyldimethylsilyl, tribenzylsilyl and triphenylsilyl.

Provided is a preparation method of the compound of formula (XI), which comprises reacting the compound of formula (X) with $R^7$—C≡CH in the presence of a strong base, such as an alkyl lithium or an alkyl Grignard reagent, to give the compound of formula (XI),

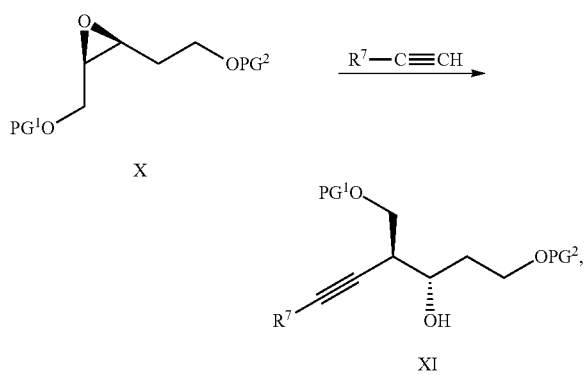

wherein $PG^1$, $PG^2$ and $R^7$ are defined as above. According to an embodiment of the present invention, the reaction may be carried out in the presence of a catalyst. For example, the catalyst may be selected from one, two or more of Lewis acids such as boron trifluoride or complexes thereof, such as boron trifluoride or boron trifluoride methanol complex, boron trifluoride diethyl ether complex, boron trifluoride acetonitrile complex, boron trifluoride tetrahydrofuran complex and boron trifluoride ethylamine complex;

according to an embodiment of the present invention, the molar ratio of the compound of formula (X) to $R^7$—C≡CH may be 1:(1-10), such as 1:(1-5), such as 1:(1.5-3), such as 1:2; the molar ratio of the compound of formula (X) to the alkyl lithium may be 1:(1-10), such as 1:(1-5), such as 1:(1.5-3), such as 1:2; the molar ratio of the compound of formula (X) to the catalyst may be 1:(1-10), such as 1:(1-5), such as 1:(1.5-3), such as 1:2;

According to the embodiment, the strong base may be alkyl lithium, such as one, two or more of methyl lithium, ethyl lithium, propyl lithium, isopropyl lithium, n-butyl lithium, sec-butyl lithium, tert-butyl lithium, pentyl lithium and hexyl lithium; or an alkyl Grignard reagent such as one, two or more of methyl, ethyl, propyl, isopropyl, n-butyl, sec-butyl, tert-butyl, pentyl, hexyl and phenyl Grignard reagents and the like, wherein the halogen contained in the Grignard reagent can be chlorine, bromine or iodine.

According to an embodiment of the present invention, the reaction may be carried out in the presence of an organic solvent. The organic solvent may be an inert organic solvent, which may be selected from organic solvents that are inert under the reaction conditions and particularly do not chemically react with the starting materials and products, including, for example, a mixture of one, two or more selected from: hydrocarbon solvents such as benzene, toluene, xylene, hexane and cyclohexane; halogenated hydrocarbon solvents such as dichloromethane, trichloromethane, 1,2- dichloroethane and chlorobenzene; or other solvents, such as N,N-dimethylformamide (DMF), dimethyl sulfoxide (DMSO), N-methylpyrrolidone (NMP), acetonitrile or pyridine; ether solvents such as diethyl ether and tetrahydrofuran. According to an embodiment of the present invention, the temperature of the reaction may be −80° C. to 0° C., such as −60° C. to −30° C.; the time of the reaction may be 0.5-5 h, such as 1-3 h.

According to an embodiment of the present invention, in the above preparation method of the above compound of formula (XI), the product further comprises a compound of formula (XIa) shown below:

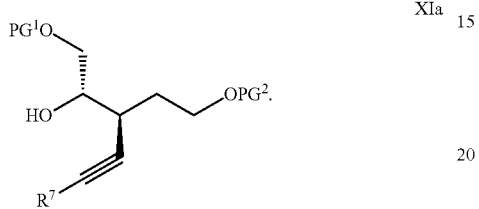

XIa

According to an embodiment of the present invention, in the product of the above preparation method of the compound of formula (XI), except for the compound of formula (XIa), the content of other isomers of the compound of formula (XI) is ≤0.1%.

According to an embodiment of the present invention, the above preparation method of the compound of formula (XI) further comprises separating the compounds of formulae XI and XIa by chromatographic means (e.g., column chromatography).

According to an exemplary embodiment, a packing medium of the column chromatography may be silica gel; an eluent for the column chromatography may be a mixture of petroleum ether and ethyl acetate, and the volume ratio of the mixture may be (5-20):1, such as 10:1. Preferably, the content of the compound of formula (XIa) in the product of the above preparation method of the compound of formula (XI) is ≤0.1% after chromatographic separation.

The present invention also provides a compound of formula (XI), (XII), (XIII), (XIV), (XV) or (XVI) shown below:

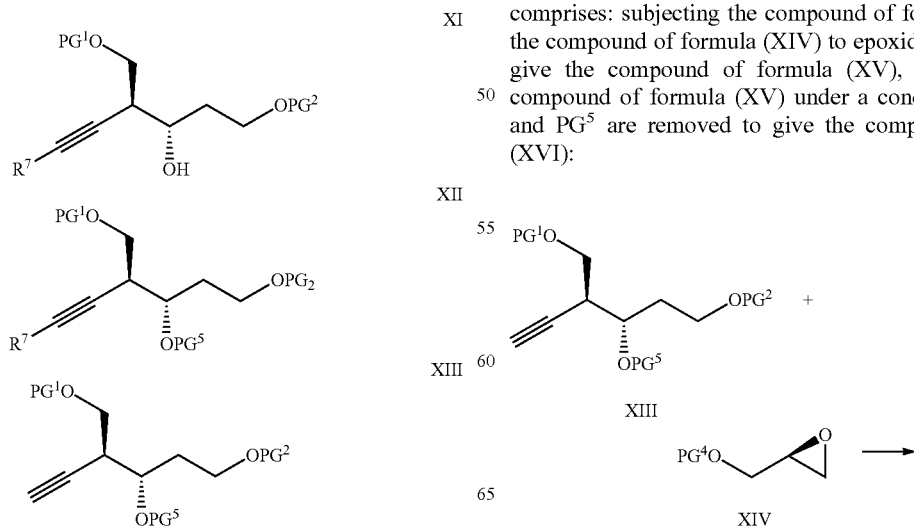

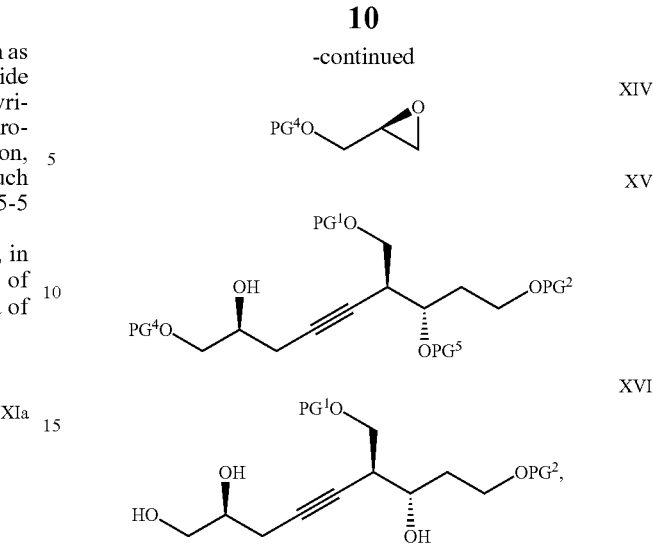

wherein, $PG^1$, $PG^2$ and $R^7$ are defined as above; $PG^4$ and $PG^5$ are the same or different and are each independently selected from the hydroxyl protecting groups described above;

with the proviso that either of the $PG^4$ and the $PG^5$ is not the same as either of the $PG^1$ and the $PG_2$, and the $PG^1$ and the $PG^2$ do not react under a condition where the $PG^4$ and the $PG^5$ are removed.

According to an embodiment of the present invention, the $PG^4$ and the $PG^5$ are the same or different, and are each independently selected from silyl; for example, the $PG^4$ and the $PG^5$ are the same or different, and are each independently selected from trialkylsilyl (e.g., trimethylsilyl, triethylsilyl or triisopropylsilyl), tert-butyldiphenylsilyl, tert-butyldimethylsilyl, tribenzylsilyl and triphenylsilyl, and the $PG^1$ and the $PG_2$ are the same or different, and are each independently selected from hydroxyl protecting groups except for silyl, such as alkyl, alkenyl, cycloalkyl, aryl, heteroaryl, heterocyclyl, tetrahydropyranyl, acyl, sulfonyl, alkyloxycarbonyl, arylalkyloxycarbonyl, groups obtained by removing OH groups from inorganic acids, and phosphinothioyl.

The present invention also provides a preparation method of a compound of formula (XVI) shown below, which comprises: subjecting the compound of formula (XIII) and the compound of formula (XIV) to epoxide ring-opening to give the compound of formula (XV), and reacting the compound of formula (XV) under a condition where $PG^4$ and $PG^5$ are removed to give the compound of formula (XVI):

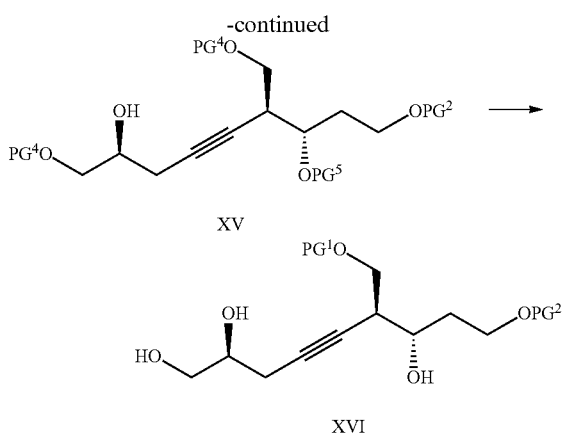

XV

XVI wherein PG¹, PG², PG⁴ and PG⁵ are defined as above.

Preferably, the reaction of the compound of formula (XIII) with the compound of formula (XIV) is carried out in the presence of n-butyl lithium and $BF_3Et_2O$.

According to an exemplary embodiment of the present invention, the conditions for removing PG⁴ and PG⁵ may be selected from conditions known in the art for removing such hydroxyl protecting groups; for example, the removal of silyl may be carried out under acidic conditions (e.g., HCl-containing organic solvent systems; acetic acid and tetrahydrofuran systems; trifluoroacetic acid, hydrogen fluoride and pyridine systems; or potassium fluoride and acetonitrile systems) or in the presence of ammonium fluoride compounds (e.g., tetramethylammonium fluoride, tetraethylammonium fluoride or tetrabutylammonium fluoride).

According to a preferred embodiment of the present invention, when the compound of formula (XIV) used has an enantiomeric purity of less than 99.9%, the crude product of the compound of formula (XVI) can be purified by recrystallization so that it contains the compound of formula (XVIa) shown below in an amount of ≤0.1%.

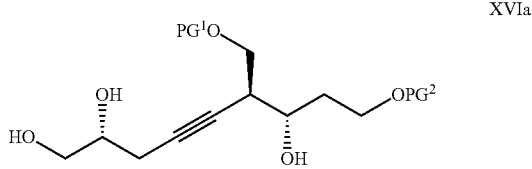

XVIa

According to an embodiment of the present invention, the recrystallization comprises: dissolving the crude product of the compound of formula (XVI) containing the compound of formula (XVIa) in a good solvent, heating to dissolve the crude compound, adding a poor solvent, and cooling to give the purified compound of formula (XVI).

According to an exemplary embodiment of the present invention, the good solvent may be any one of methanol, isopropanol, ethanol, acetonitrile, ethyl acetate, tetrahydrofuran, methyl tert-butyl ether, isopropyl ether, chloroform, acetone and dioxane; the poor solvent may be any one of petroleum ether, n-octane, cyclohexane, n-hexane, heptane, benzene and toluene; the weight-volume ratio of the crude product of the compound of the formula (XVI) to the good solvent and the poor solvent may be 1 g:(1-5) mL:(1-5) mL, such as 1 g:(1-2) mL:(1-2) mL; the recrystallization may be repeated as many times as necessary, such as 1-3 times.

According to an exemplary embodiment of the present invention, the compound of formula (XIII) may be prepared by one or more of the following steps:

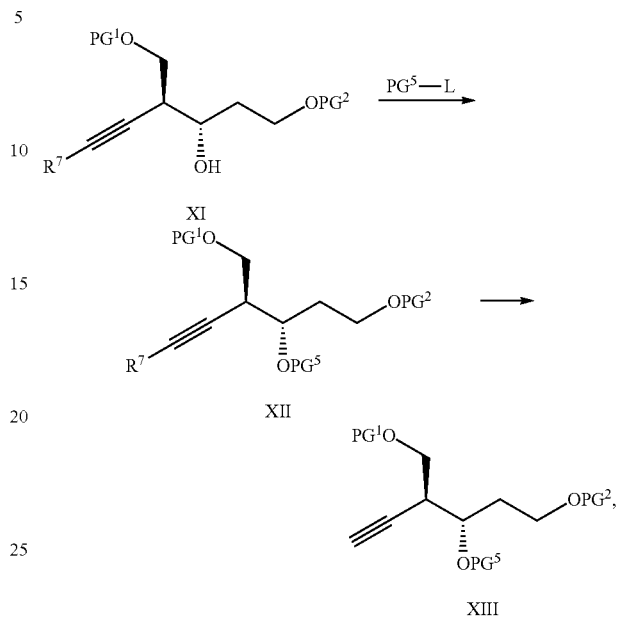

XI

XII

XIII wherein, PG¹, PG², PG⁵ and R⁷ are defined as above, and L is a leaving group, such as OTS, OMS, OTf, Cl, Br and I.

The present invention also provides a compound of formula XIX shown below:

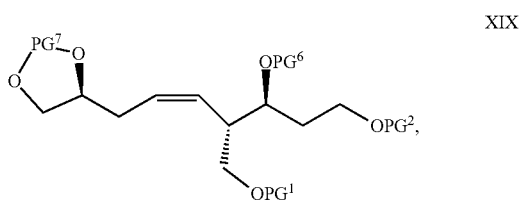

XIX wherein PG¹ and PG² are defined as above; PG⁶ is independently selected from substituted or unsubstituted aromatic acyl, such as substituted or unsubstituted benzoyl and naphthoyl. PG⁷ is an o-dihydroxyl protecting group. Preferably, the o-dihydroxyl protecting group, together with oxygen to which it is bound, forms cyclic acetals and ketals; cyclosilylene derivatives; and cyclic carbonates and cyclic borates. Acetal refers to —CHR—, ketal refers to —CR₂—, cyclic carbonate refers to —OC(O)O—, and cyclic carbonate refers to OBRO—, wherein R is H, alkyl, alkenyl, aryl or aralkyl.

According to an embodiment of the present invention, the o-dihydroxyl protecting group may be selected from substituted or unsubstituted alkylene, cycloalkylene, silylene and acyl. For example, the o-dihydroxyl protecting group may be substituted or unsubstituted methylene, ethylidene, isopropylidene, cyclohexylene, cyclopentylene, phenylmethylene, diphenylmethylene, p-methoxyphenylmethylene, 2,4,6-trimethylphenylmethylene, di-tert-butylsilylene, 1,1,3,3-tetraisopropylsiloxane, carbonyl, etc.

According to an embodiment of the present invention, the compound of formula (XIX) can be prepared by the following steps:

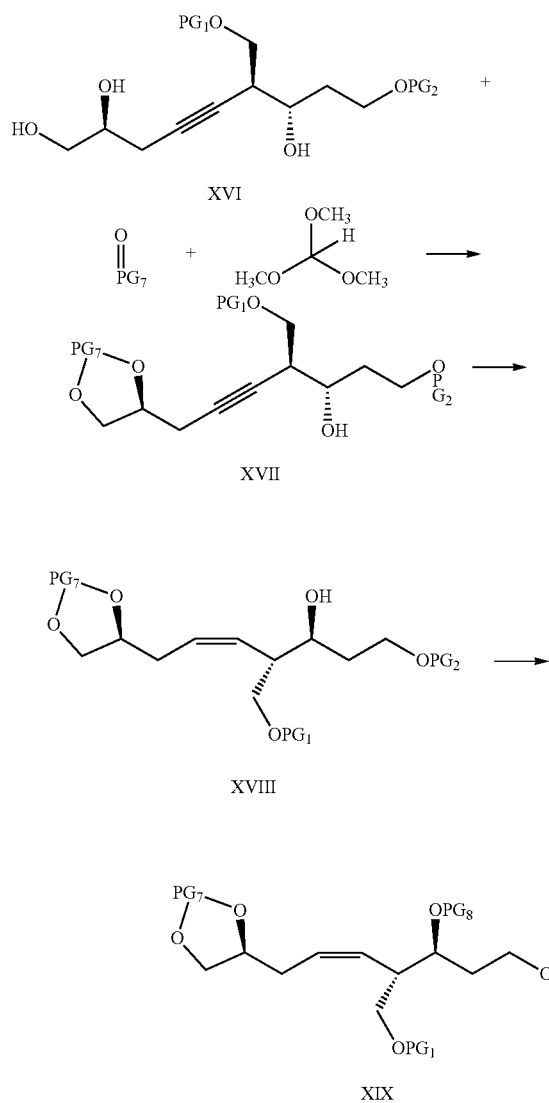

XVI

XVII

XVIII

XIX wherein, $PG^1$, $PG^2$ and $PG^6$ are defined as above;

$PG^7$ is selected from substituted or unsubstituted alkylene, for example, methylene substituted with dialkyl, such as methylene substituted with diethyl.

Preferably, the compound of formula (XVII) is obtained by the reaction of the compound of formula (XVI) with

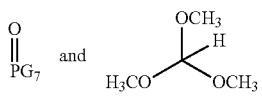

in the presence of scandium trifluoromethanesulfonate; the compound of formula (XVIII) is obtained by hydrogenation reduction of the compound of formula (XVII) in the presence of a Lindlar catalyst; the compound of formula (XIX) is obtained by the reaction of the compound of formula (XVIII) with $PG^6X$ in the presence of DMAP and pyridine; wherein $PG^6$, $PG^7$ and X are defined as above.

The present invention also provides a compound of formula (XX):

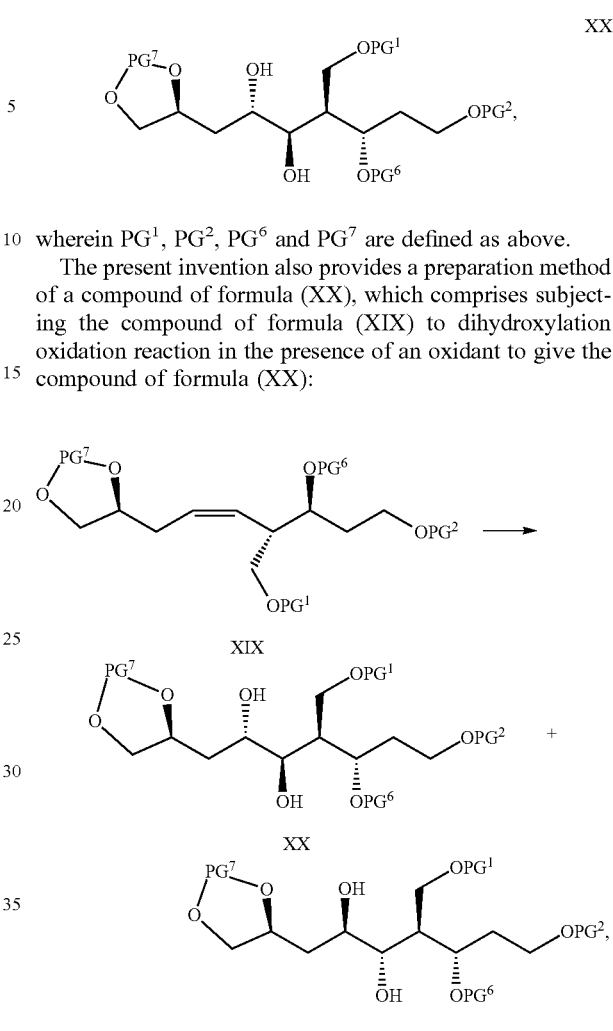

XX

XIX

XX

XXa wherein $PG^1$, $PG^2$, $PG^6$ and $PG^7$ are defined as above.

The present invention also provides a preparation method of a compound of formula (XX), which comprises subjecting the compound of formula (XIX) to dihydroxylation oxidation reaction in the presence of an oxidant to give the compound of formula (XX):

wherein $PG^1$, $PG_2$, $PG^6$ and $PG^7$ are defined as above.

According to an embodiment of the present invention, the oxidant may be selected from one or more of potassium permanganate, sodium periodate, hydrogen peroxide, potassium ferricyanide and N-methyl-N-morpholine oxide (NMO). According to an embodiment of the present invention, a co-oxidant may be added in the reaction as required, and the co-oxidant may be any one of osmium tetroxide and potassium osmate. According to an embodiment of the present invention, the reaction may be carried out under the catalysis of a base, which may be one or more of 1,4-diazabicyclo[2.2.2]octane (DABCO), triethylamine and N,N-diisopropylethylamine. According to an embodiment of the present invention, the molar ratio of the compound of formula (XIX) to the oxidant is 1:(1-5), preferably 1:(1-3); the molar ratio of the compound of formula (XIX) to the co-oxidant is 1:(0.005-0.15), preferably 1:(0.005-0.1); the molar ratio of the compound of formula (XIX) to the base is 1:(0.4-2), preferably 1:(0.5-1.5). According to an embodiment of the present invention, the reaction may be carried out in a mixed solvent, wherein the mixed solvent is a mixture of an organic solvent and water, for example, the mixed solvent is selected from one of the following systems: tert-butanol/water, acetone/water and acetonitrile/water; in the mixed solvent, the volume ratio of the organic solvent to water may be (1:5)-(5:1), such as (2-2.5):(2.5-2); according to an embodiment of the present invention, the ratio of the weight of the compound of formula (XIX) to the total volume of the mixed solvent may be 1 g:(2-50 mL), such as 1 g:4 mL or 1 g:22.2 mL; according to an embodiment of the present invention, the temperature of the reaction is −10° C. to 50° C., such as 35-45° C.; the time of the reaction may be 10-60 h, such as 24 h.

According to a preferred embodiment of the present invention, the stereoselectivity of the reaction is greatly improved by adopting PG⁶ that is different from the prior art and optimizing the time of reaction, the temperature of reaction and the reaction solvent. In the product obtained by the reaction, the content of the target product, namely the compound of formula (XX), can be higher than 95%, and the content of the byproduct, namely the compound of formula (XXa), is lower than 5%. Correspondingly, when the prior art is utilized (PG⁶ is acetyl), the content of the target product, namely the compound of formula (XX), is less than 85%. The technology used herein greatly reduces the proportion of a byproduct in the product, and significantly lowers the difficulty in separating the compound of formula (XX) and subsequent derivative products thereof, such as a compound of formula (XXIIIa).

The present invention also provides a preparation method of a compound of formula (XXIII) shown below, which comprises one, two or more of the preparation methods of the compounds of formulae (IX), (X), (XI), (XVI) and (XX) described above:

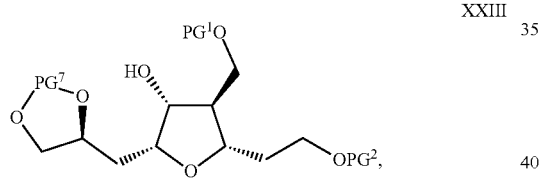

XXIII wherein PG¹, PG² and PG⁷ are defined as above.

Preferably, the preparation method of the compound of formula (XXIII) further comprises separating a obtained product by column chromatography. Preferably, in the preparation method of the compound of formula (XXIII), the content of the compound of formula (XXIIIa) shown as the formula below is ≤0.1% in a product obtained after column chromatography separation,

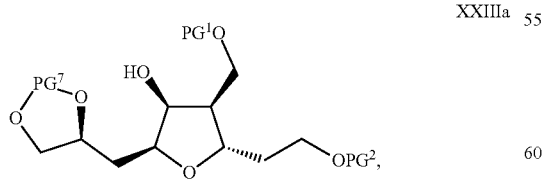

XXIIIa wherein PG¹, PG² and PG⁷ are defined as above.

By way of example, the present invention also provides a preparation method of a compound of formula 23 shown below, which comprises at least one of the following steps:

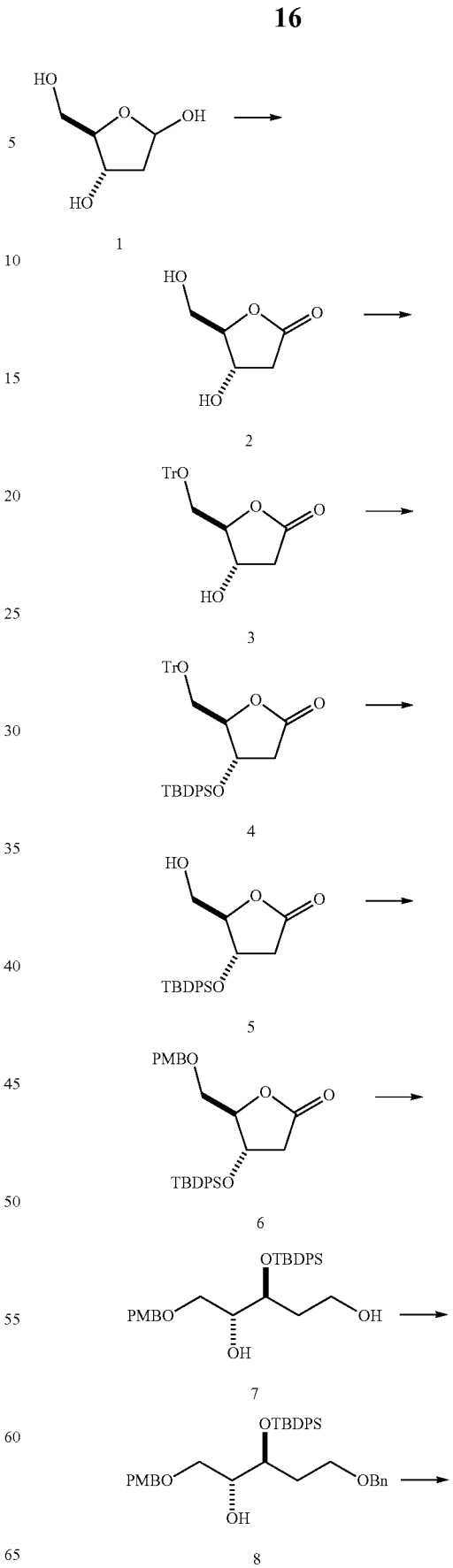

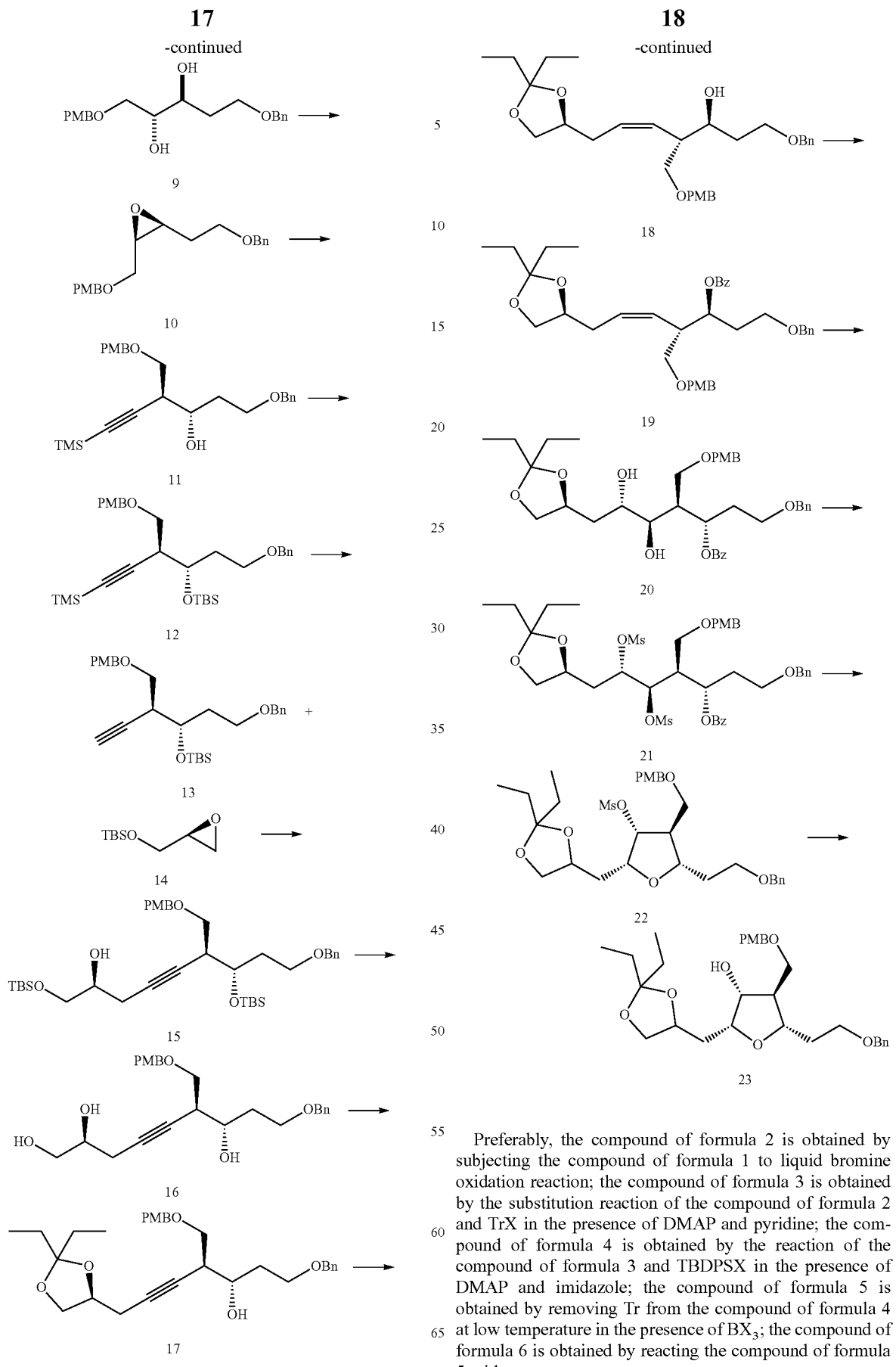

Preferably, the compound of formula 2 is obtained by subjecting the compound of formula 1 to liquid bromine oxidation reaction; the compound of formula 3 is obtained by the substitution reaction of the compound of formula 2 and TrX in the presence of DMAP and pyridine; the compound of formula 4 is obtained by the reaction of the compound of formula 3 and TBDPSX in the presence of DMAP and imidazole; the compound of formula 5 is obtained by removing Tr from the compound of formula 4 at low temperature in the presence of $BX_3$; the compound of formula 6 is obtained by reacting the compound of formula 5 with

the compound of formula 7 is obtained by ring opening of the compound of formula 6 in the presence of borane dimethyl sulfide; the compound of the formula 8 is obtained by reacting the compound of formula 7 with BnX and

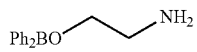

in the presence of a base and potassium iodide; the compound of formula 9 is obtained by removing TBDPS from the compound of formula 8 in the presence of TBAF; the reaction of the compound of formula 13 with the compound of formula 14 is carried out in the presence of n-butyl lithium and $BF_3Et_2O$; the compound of formula 17 is obtained by the reaction of the compound of formula 16 with pentanone and

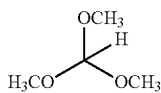

in the presence of scandium trifluoromethanesulfonate; the compound of formula 18 is obtained by hydrogenation reduction of the compound of formula 17 in the presence of a Lindlar catalyst; the compound of formula 19 is obtained by the reaction of the compound of formula 18 with BzX in the presence of DMAP and pyridine; the compound of formula 21 is obtained by the reaction of the compound of formula 20 with MsX in the presence of DMAP and a base; the compound of formula 22 is obtained by ring closing reaction of the compound of formula 21 in the presence of a base; the compound of formula 23 is obtained by removing an Ms protecting group from the compound of formula 22 in the presence of an alkyl Grignard reagent; wherein all the X are the same or different and are each independently selected from halogen.

The present invention also provides a method for preparing eribulin, an analog thereof, or a C27-C35 portion thereof, which comprises using any one of the compounds of formulae (I) to (XXIII) described above, and/or using one or more preparation methods described above.

The present invention also provides use of any one of the compounds of formulae (I) to (XXIII) described above in preparing eribulin, an analogue thereof, or a C27-C35 portion thereof.

Terminology and Definitions

Unless otherwise stated, the definitions of groups and terms described in the specification and claims of the present application, including definitions thereof as examples, exemplary definitions, preferred definitions, definitions documented in tables, definitions of specific compounds in the examples, and the like, may be arbitrarily combined and incorporated with each other. The definitions of groups and the structures of the compounds in such combinations and incorporations should fall within the scope of the present specification.

Unless otherwise stated, a numerical range set forth in the description and claims shall be construed as at least including each specific integer within the range. For example, the numerical range "1-40" shall be construed as at least including each integer value in the numerical range "1-10", i.e., 1, 2, 3, 4, 5, 6, 7, 8, 9 and 10, and each integer value in the numerical range "11-40", i.e., 11, 12, 13, 14, 15, . . . , 35, 36, 37, 38, 39 and 40. If possible, when certain numerical ranges are defined as "numbers", it shall be construed as including both endpoints of the range, each integer within the range, and each decimal within the range. For example, "numbers of 0-10" shall be construed as including not only each of integers 0, 1, 2, 3, 4, 5, 6, 7, 8, 9 and 10, but also at least the sums of each integer independently and 0.1, 0.2, 0.3, 0.4, 0.5, 0.6, 0.7, 0.8 or 0.9. It should be understood that when one, two or more are described herein, "more" shall mean an integer ≥3, such as 3, 4, 5, 6, 7, 8, 9 or 10.

The term "alkyl" preferably refers to a linear or branched saturated monovalent hydrocarbyl having 1-40 carbon atoms, and is preferably C1-10 alkyl. "C1-10 alkyl" preferably refers to a linear or branched saturated monovalent hydrocarbyl having 1, 2, 3, 4, 5, 6, 7, 8, 9 or 10 carbon atoms. The alkyl is, for example, methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethylbutyl, or isomers thereof. In particular, the group has 1, 2, 3, 4, 5 or 6 carbon atoms ("$C_{1-6}$ alkyl"), such as methyl, ethyl, propyl, butyl, isopropyl, isobutyl, sec-butyl or tert-butyl, more particularly, the group has 1, 2 or 3 carbon atoms ("$C_{1-3}$ alkyl"), such as methyl, ethyl, n-propyl or isopropyl.

The term "alkenyl" preferably refers to a linear or branched monovalent hydrocarbyl comprising one or more double bonds and having 2-40 carbon atoms, and is preferably "C2.6 alkenyl". "C2.4 alkenyl" preferably refers to a linear or branched monovalent hydrocarbyl comprising one or more double bonds and having 2, 3, 4, 5 or 6 carbon atoms, in particular 2 or 3 carbon atoms ("C2-3alkenyl"); it should be understood that in the case that the alkenyl comprises more than one double bond, the double bonds can be separated from one another or conjugated. The alkenyl is, for example, vinyl, allyl, (E)-2-methylvinyl, (Z)-2-methylvinyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (F)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl or 1-isopropylvinyl.

The term "cycloalkyl" refers to a saturated or unsaturated monovalent monocyclic or bicyclic hydrocarbon ring or bridged cycloalkane having 3-40 carbon atoms, and is preferably a "$C_{3-10}$ cycloalkyl". The term "$C_{3-10}$ cycloalkyl" refers to a saturated monovalent monocyclic or bicyclic hydrocarbon ring or bridged cycloalkane having 3, 4, 5, 6, 7, 8, 9 or 10 carbon atoms. The $C_{3-10}$ cycloalkyl may be a monocyclic hydrocarbyl such as cyclopropyl, cyclobutyl, cyclopentyl, cyclohexyl, cycloheptyl, cyclooctyl, cyclononyl or cyclodecyl, or may be a bicyclic hydrocarbyl such as a decahydronaphthalene ring.

The term "heterocyclyl" preferably refers to a saturated or unsaturated monovalent monocyclic or bicyclic hydrocarbon ring or bridged cycloalkane comprising 1-5 heteroatoms independently selected from N, O and S, and it is a non-aromatic cyclic group comprising a total of 3-20 (e.g., 3, 4, 5, 6, 7, 8, 9, 10, etc.) ring atoms and is preferably "3-10-membered heterocyclyl". The term "3-10 membered heterocyclyl" refers to a saturated monovalent monocyclic or bicyclic hydrocarbon ring or bridged cycloalkane comprising 1-5, preferably 1-3, heteroatoms selected from N, O and S. The heterocyclyl may be connected to the rest of the molecule through any one of the carbon atoms or the nitrogen atom (if present). In particular, the heterocyclyl may include, but is not limited to: 4 membered rings such as azetidinyl or oxetanyl; 5 membered rings such as tetrahydrofuranyl, dioxolyl, pyrrolidinyl, imidazolidinyl, pyrazolidinyl or pyrrolinyl; 6 membered rings such as tetrahydropyranyl, piperidinyl, morpholinyl, dithianyl, thiomorpholinyl, piperazinyl or trithianyl; or 7 membered rings such as diazepanyl. Optionally, the heterocyclyl may be benzo-fused. The heterocyclyl may be bicyclic, such as but not limited to a 5,5 membered ring such as a hexahydrocyclopenta[c]pyrrol-2(1H)-yl ring, or a 5,6 membered bicyclic ring such as a hexahydropyrrolo[1,2-a]pyrazin-2(1H)-yl ring. The ring comprising nitrogen atoms may be partially unsaturated, i.e., it may comprise one or more double bonds, such as but not limited to 2,5-dihydro-1H-pyrrolyl, 4H-[1,3,4]thiadiazinyl, 4,5-dihydrooxazolyl or 4H-[1,4]thiazinyl, or it may be benzo-fused, such as but not limited to dihydroisoquinolyl. According to the present invention, the heterocyclyl is non-aromatic.

The term "aryl" refers to an aromatic or partially aromatic monovalent monocyclic, bicyclic or tricyclic hydrocarbon ring having 6-20 carbon atoms, and is preferably "$C_{6-14}$ aryl". The term "$C_{6-14}$ aryl" refers to preferably an aromatic or partially aromatic monovalent monocyclic, bicyclic or tricyclic hydrocarbon ring having 6, 7, 8, 9, 10, 11, 12, 13 or 14 carbon atoms ("C6-14 aryl"), in particular a ring having 6 carbon atoms ("$C_6$ aryl"), such as phenyl; or a biphenyl, a ring having 9 carbon atoms ("$C_9$ aryl") such as indanyl or indenyl, a ring having 10 carbon atoms ("$C_{6-14}$ aryl") such as tetrahydronaphthyl, dihydronaphthyl or naphthyl, a ring having 13 carbon atoms ("$C_{10}$ aryl") such as fluorenyl, or a ring having 14 carbon atoms ("$C_{14}$ aryl") such as anthracenyl. When the $C_{6-20}$ aryl is substituted, it may be monosubstituted or polysubstituted. In addition, the substitution site is not limited, and may be, for example, ortho-, para- or meta-substituted.

The term "heteroaryl" preferably refers to an aromatic monovalent monocyclic, bicyclic or tricyclic ring which has 5-20 ring atoms, comprises 1-5 heteroatoms independently selected from N, O and S, and is, for example, "5-14 membered heteroaryl". The term "5-14 membered heteroaryl" refers to an aromatic monovalent monocyclic, bicyclic or tricyclic ring which has 5, 6, 7, 8, 9, 10, 11, 12, 13 or 14 ring atoms, in particular 5, 6, 9 or 10 carbon atoms, comprises 1-5, preferably 1-3 heteroatoms independently selected from N, O and S, and may be benzo-fused in each case. In particular, the heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl and the like and benzo derivatives thereof, such as benzofuranyl, benzothienyl, benzoxazolyl, benzoisoxazolyl, benzimidazolyl, benzotriazolyl, indazolyl, indolyl, and isoindolyl; or pyridinyl, pyridazinyl, pyrimidinyl, pyrazinyl, triazinyl and the like and benzo derivatives thereof, such as quinolyl, quinazolinyl, and isoquinolyl; or azocinyl, indolizinyl, purinyl and the like and benzo derivatives thereof; or cinnolinyl, phthalazinyl, quinazolinyl, quinoxalinyl, naphthyridinyl, pteridinyl, carbazolyl, acridinyl, phenazinyl, phenothiazinyl, phenoxazinyl, and the like. When the 5-20 membered heteroaryl is linked to another group to form the compound of the present invention, the carbon atoms on the 5-20 membered heteroaryl ring may be linked to another group, or the heteroatoms on the 5-20 membered heteroaryl ring may be linked to another group. When the 5-20 heteroaryl is substituted, it may be mono-substituted or polysubstituted. In addition, the substitution site is not limited. For example, hydrogen attached to a carbon atom on a heteroaryl ring may be substituted, or hydrogen attached to a heteroatom on a heteroaryl ring may be substituted.

Unless otherwise stated, the heterocyclyl, heteroaryl or heteroarylene includes all possible isomeric forms thereof, e.g., positional isomers thereof. Thus, for some illustrative non-limiting examples, forms that involving substitutions at or bonding to other groups at one, two or more of positions 1-, 2-, 3-, 4-, 5-, 6-, 7-, 8-, 9-, 10-, 11-, 12-, etc. (if present) are included, including pyridin-2-yl, pyridinylene-2-yl, pyridin-3-yl, pyridinylene-3-yl, pyridin-4-yl and pyridinylene-4-yl; thienyl or thienylene, such as thien-2-yl, thien-2-ylene, thien-3-yl, and thien-3-ylene; pyrazol-1-yl, pyrazol-3-yl, pyrazol-4-yl and pyrazol-5-yl.

The above alkyl, alkenyl, cycloalkyl, heterocyclyl, aryl and heteroaryl may be substituted with halogen, hydroxyl, amino (substituted or unsubstituted amino, e.g., —N($C_{1-6}$alkyl)$_2$, or —NH$C_{1-6}$alkyl), nitro, cyano, carboxyl, azido, alkyl, alkoxy, cycloalkyl, acyl, aryl or heteroaryl.

The term "halogen" refers to fluorine, chlorine, bromine and iodine.

Unless otherwise stated, the definitions of terms used herein are also applicable to groups comprising the terms. For example, the definition of $C_{1-6}$ alkyl is also applicable to $C_{1-6}$ alkyloxy, —N($C_{1-6}$ alkyl)$_2$, —NH$C_{1-6}$ alkyl, —S(O)$_2$—$C_{1-6}$ alkyl or the like.

The "hydroxyl protecting group" used herein refers to a group introduced during synthesis to protect hydroxyl for the purpose of avoiding undesirable chemical reactions of the hydroxyl under reactive conditions; the hydroxyl protecting group will be removed in subsequent synthetic steps to restore the hydroxyl. Exemplary hydroxyl protecting groups include, but are not limited to:

substituted or unsubstituted alkyl, such as methyl, tert-butyl and other $C_1$-$C_6$ alkyl groups; methoxymethyl, methylthiomethyl, benzyloxymethyl, tert-butoxymethyl, 2-methoxyethoxymethyl, 2,2,2-trichloroethoxymethyl, bis(2-chloroethoxy)methyl and 2-(trimethylsilyl)ethoxymethyl; 1-ethoxyethyl, 1-methyl-1-methoxyethyl, 1-isopropoxyethyl, 2,2,2-trichloroethyl and 2-methoxyethyl; 1-hydroxyalkyl groups such as 1-hydroxyethyl, 1-hydroxyhexyl, 1-hydroxydecyl, 1-hydroxyhexadecyl and 1-hydroxy-1-phenylmethyl; substituted or unsubstituted arylalkyl groups such as benzyl, methoxybenzyl, 2,6-dichlorobenzyl, 3-bromobenzyl, 2-nitrobenzyl and triphenylmethyl;

substituted or unsubstituted heteroarylalkyl; substituted or unsubstituted heterocyclylalkyl;

substituted or unsubstituted alkenyl, such as allyl;

substituted or unsubstituted cycloalkyl, such as cyclohexyl;

substituted or unsubstituted aryl, such as phenyl or 2,4-dinitrophenyl;

substituted or unsubstituted heteroaryl;

substituted or unsubstituted heterocyclyl;

substituted or unsubstituted tetrahydropyranyl, substituted or unsubstituted tetrahydrofuranyl, and other groups capable of forming an acetal or hemiacetal group with hydroxyl;

substituted or unsubstituted acyl, such as formyl; substituted or unsubstituted alkylcarbonyl, such as methylcarbonyl, ethylcarbonyl, propylcarbonyl, butylcarbonyl, isobutylcarbonyl, pentylcarbonyl, neopentylcarbonyl, hexylcarbonyl, heptylcarbonyl, octylcarbonyl, decylcarbonyl, nonylcarbonyl, dodecylcarbonyl, tetradecylcarbonyl, hexadecylcarbonyl, octadecylcarbonyl and other substituted or unsubstituted alkylcarbonyl groups; acetoacetyl; substituted or unsubstituted cycloalkylcarbonyl, such as cyclopentylcarbonyl or cyclohexylcarbonyl; substituted or unsubstituted arylacyl, such as benzoyl or naphthoyl; substituted or unsubstituted carbamoyl, such as carbamoyl, methylcarbamoyl and phenylcarbamoyl;

substituted or unsubstituted sulfonyl, such as methanesulfonyl, ethanesulfonyl, trifluoromethanesulfonyl, benzenesulfonyl, p-toluenesulfonyl and naphthalenesulfonyl;

substituted or unsubstituted alkyloxycarbonyl, such as methoxycarbonyl, ethoxycarbonyl, tert-butoxycarbonyl and other $C_1$-$C_6$ alkoxycarbonyl groups;

substituted or unsubstituted arylalkyloxycarbonyl, such as benzyloxycarbonyl and p-methoxybenzyloxycarbonyl;

groups obtained by removing OH groups from inorganic acids (such as sulfuric acid, nitric acid, phosphoric acid and boric acid);

phosphinothioyl, such as a dialkylphosphinothioyl (e.g., dimethylphosphinothioyl) or diarylphosphinothioyl (e.g., diphenylphosphinothioyl); and silyl, such as trialkylsilyl (e.g., trimethylsilyl, triethylsilyl or triisopropylsilyl), tert-butyldiphenylsilyl, tert-butyldimethylsilyl, tribenzylsilyl and triphenylsilyl, wherein alkyl is as defined above.

The "hydroxyl protecting group" of the present invention, together with an oxygen atom to which it is bound, may form the following specific examples: formate, benzoylformate, chloroacetate, trifluoroacetate, methoxyacetate, triphenylmethoxyacetate, p-chlorophenoxyacetate, 3-phenylpropionate, 4-oxovalerate, 4,4-(ethylenedithio)valerate, pivalate(pivaloyl), crotonate, 4-methoxycrotonate, benzoate, p-benzylbenzoate and 2,4,6-trimethylbenzoate; or carbonate of the following groups: methyl, 9-fluorenylmethyl, ethyl, 2,2,2-trichloroethyl, 2-(trimethylsilyl)ethyl, 2-(phenylsulfonyl)ethyl, vinyl, propenyl, and p-nitrophenyl; the following silyl ethers: trimethylsilyl ether, triethylsilyl ether, tert-butyldimethylsilyl ether, tert-butyldiphenylsilyl ether, and triisopropylsilyl ether; the following alkyl ethers: methyl ether, benzyl ether, p-methoxybenzyl ether, 3,4-dimethoxybenzyl ether, trityl ether, tert-butyl ether, allyl ether and allyloxycarbonyl ether; the following alkoxyalkyl ethers: methoxymethyl ether, methylthiomethyl ether, (2-methoxyethoxy)methyl ether, benzyloxymethyl ether, β-(trimethylsilyl)ethoxymethyl ether and tetrahydropyranyl ether; the following arylalkyl ethers: benzyl ether, 2,6-dichlorobenzyl ether, p-cyanobenzyl ether, and 2- and 4-picolyl ether.

The "o-dihydroxyl protecting group" used herein refers to a group introduced during synthesis to protect o-dihydroxyl for the purpose of avoiding undesirable chemical reactions of the o-dihydroxyl under reactive conditions; the o-dihydroxyl protecting group will be removed in subsequent synthetic steps to restore the o-dihydroxyl. The dihydroxyl protecting group, together with oxygen to which it is bound, forms cyclic acetals and ketals; cyclosilylene derivatives; and cyclic carbonates and cyclic borates. Acetal refers to —CHR—, ketal refers to —CR$_2$—, cyclic carbonate refers to —OC(O)O—, and cyclic carbonate refers to OBRO—, wherein R is H, alkyl, alkenyl, aryl, or aralkyl; exemplary o-dihydroxyl protecting groups include, but are not limited to, substituted or unsubstituted groups such as alkylene (e.g., methylene, ethylidene, isopropylidene, phenylmethylene, diphenylmethylene, p-methoxyphenylmethylene or 2,4,6-trimethylphenylmethylene); cycloalkylene (e.g., cyclohexylene or cyclopentylene), di($C_{1-6}$ alkyl)silylene (e.g., di-tert-butylsilylene or 1,1,3,3-tetraisopropylsiloxane), methylborate, ethylborate, phenylboronate and 2,6-diacetamidophenylborate.

Unless otherwise stated, the solvent used herein is preferably an anhydrous solvent.

Beneficial effects of the present invention: the present invention provides an intermediate useful for the synthesis of eribulin or an analog thereof, particularly a structural fragment C27-C35 thereof, and a preparation method and use thereof. The design of the synthetic route disclosed herein changes the starting materials and route steps of the existing methods in the prior art, and the starting materials are cheap and easy to obtain, the optical purity is controllable, and steps for constructing a chiral center feature higher diastereoselectivity and yield (especially the synthetic steps of the compounds of formulae (X), (XI), (XVI) and (XV)), so that the optical purity of the final product of the structural fragment C27-C35 in eribulin or the analogue thereof is ensured. The types of impurity are few, and the impurity content of all stereoisomers can be controlled to be less than one per thousand, thus the limits specified in the control guidance principle of related impurities in APIs are met, and the subsequent steps of impurity research and purification are reduced; in a multi-step reaction, the product can be used directly in the next step without column chromatography purification, thereby reducing the purification cost; for some reactions, by-products and partial isomers can be removed only by simple post-treatment and recrystallization, so that the purity is higher than 99.9%. Therefore, not only are the purification steps simplified, but also the optical purity of the final product is ensured, and the cost of impurity synthesis and separation and purification is greatly reduced.

DETAILED DESCRIPTION

Figure 1:
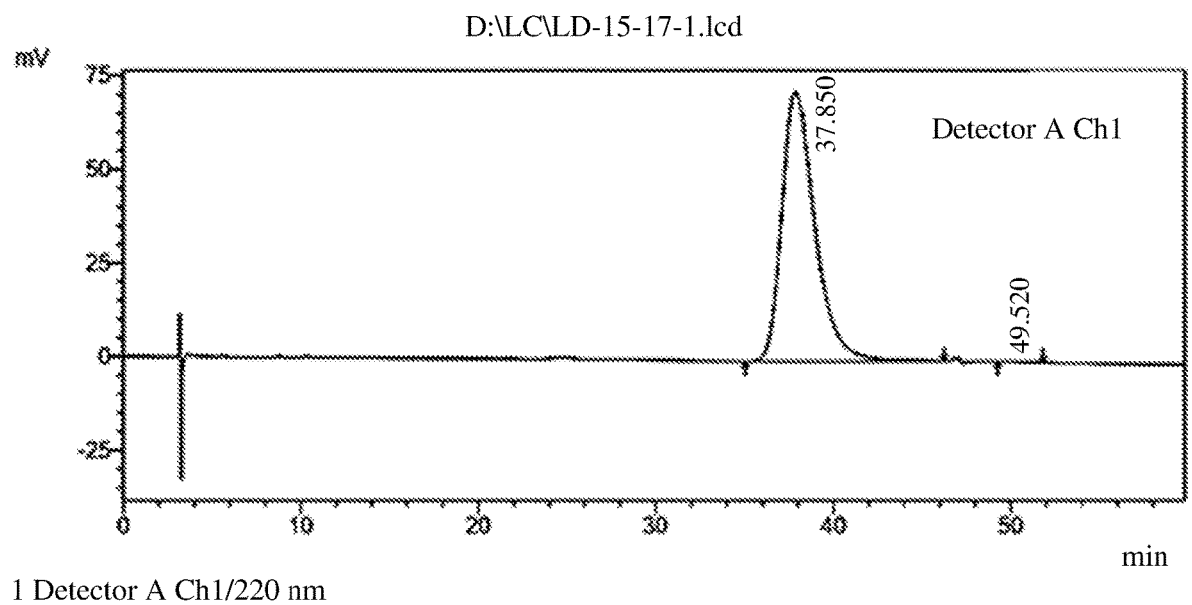
FIG. 1 is an HPLC pattern of Compound 16.

The preparation method of the present invention will be further illustrated in detail with reference to the following specific examples. It should be understood that the following examples are merely exemplary illustration and explanation of the present invention, and should not be construed as limiting the protection scope of the present invention. All techniques implemented based on the aforementioned contents of the present invention are encompassed within the protection scope of the present invention.

Unless otherwise stated, the experimental methods used in the following examples are conventional methods. Unless otherwise stated, the reagents, materials, and the like used in the following examples are commercially available.

Example 1. Synthesis of Compound 9

1.1. Synthesis of Compound 4

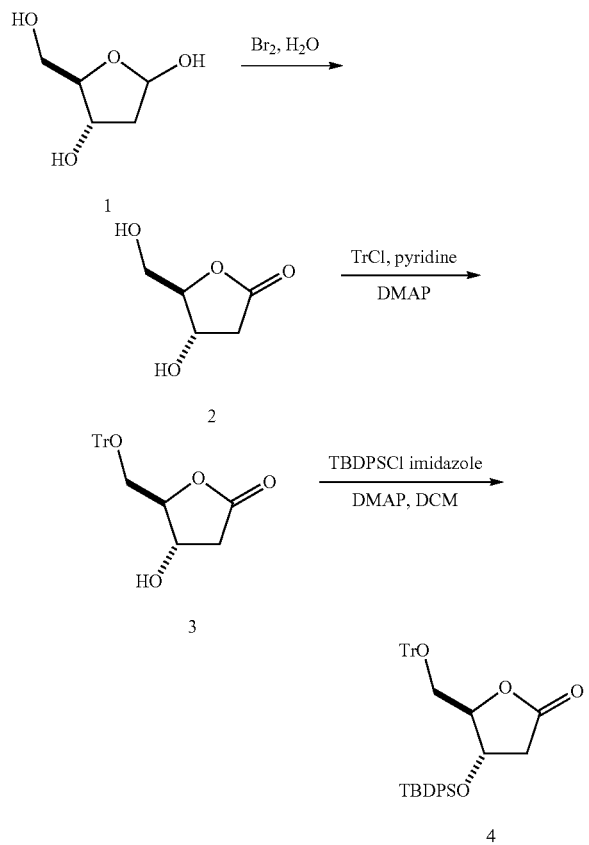

Deoxyribose 1 (100 g) was dissolved in water (400 mL), and then the mixture was cooled to about 5° C., slowly added dropwise with liquid bromine (200 g) for 3 h, heated to 30° C. and then reacted for 24 h (the disappearance of starting materials as detected by a dot plate). Post-treatment: 1) the mixture was extracted with ethyl acetate (100 mL×2) and the organic phase was at the bottom, and then ethyl acetate (50 mL) was added to extract, and the organic phase was at the top; 2) the organic phases were combined and the product contained therein was extracted with water (50 mL×2); 3) the aqueous phases were combined and the bromine was neutralized with saturated sodium thiosulfate (little amount), and then the mixture was cooled to 0° C., adjusted to pH of about 3 (the amount of solid NaOH is about 61 g), and filtered with celite; 4) the filtrate was concentrated to viscous liquid containing a small amount of solid and added with isopropanol (200 mL), and the mixture was heated to 80° C. with stirring and filtered while hot; the solid was washed with isopropanol (100 mL) and the filtrate was concentrated; the residue was dissolved in isopropanol (100 mL) and the mixture was then filtered; the solid was washed with isopropanol (40 mL), and the filtrate was concentrated; the residue was dissolved in acetone (100 mL), and the mixture was filtered; the solid was added with acetone (100 mL×2) and the mixture was heated to 80° C. for extraction; the filtrates were combined and evaporated to dryness to give a crude product of Compound 2 (about 95 g) in the form of an oil (containing a small amount of solid).

The crude product of Compound 2 (44 g) was dissolved in pyridine (200 mL) and added with trityl chloride (88 g) and 4-dimethylaminopyridine (DMAP) (4.5 g), and the mixture was heated to 50° C. and reacted overnight. Post-treatment: Pyridine was evaporated off under reduced pressure, and dichloromethane (DCM, 500 mL) was added. 1 N hydrochloric acid (300+200 mL) was added for liquid separation, saturated sodium bicarbonate (200 mL) was added for washing, and the aqueous phase was extracted each time with DCM (100 mL). The organic phases were combined, dried, filtered and concentrated, and the product was directly used in the next step.

The crude product of Compound 3 was dissolved in DCM (400 mL) and then added with imidazole (29 g) and DMAP (4.5 g). The mixture was cooled to 0° C. and added dropwise slowly with tert-butyldiphenylchlorosilane (TBDPSCl, 77 mL), and the resulting mixture was warmed to room temperature and reacted for 2-6 h. Post-treatment: Water (300 mL×2) was added, liquid separation was performed, and dichloromethane (100 mL) was added for extraction each time. The organic phases were combined, dried and concentrated. The residue was added with methanol (150 mL×2) and concentrated to dryness, and this procedure was performed twice. Then methanol (300 mL) and n-hexane (100 mL) were added. The mixture was concentrated to 200-300 mL under reduced pressure, and stirred and cooled to about 10° C., and white solid was precipitated out. The resulting mixture was filtered and the solid was washed with a small amount of cold methanol. The solid was removed and the residual solvent was evaporated off under reduced pressure to give Compound 4 (about 136 g). $^1$H NMR (500 MHz, CDCl$_3$) δ 7.58-7.25 (m, 25H), 4.41 (d, J=3.5 Hz, 1H), 4.37 (d, J=6.4 Hz, 1H), 3.32 (dd, J=10.6, 3.2 Hz, 1H), 2.88 (dd, J=17.8, 6.6 Hz, 1H), 2.70 (dd, J=10.7, 3.0 Hz, 1H), 2.55 (dd, J=17.8, 1.8 Hz, 1H), 1.07 (s, 9H).

1.2. Synthesis of Compound 7

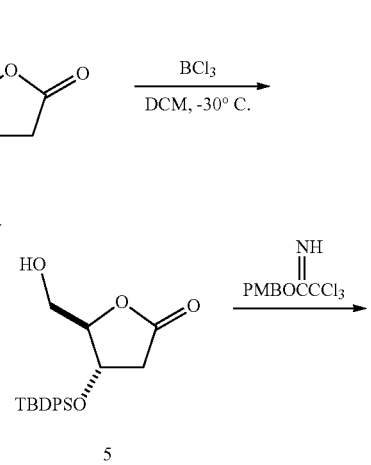

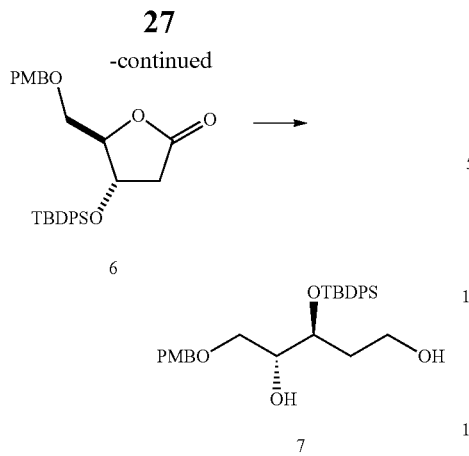

5

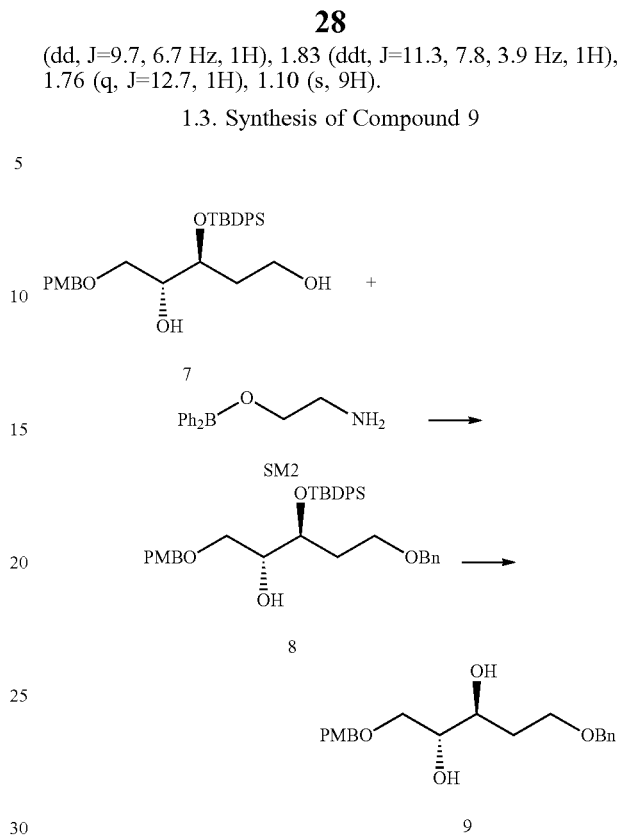

Compound 4 (286 g) was dissolved in dichloromethane, and then the mixture was cooled to −20° C., added dropwise slowly with boron trichloride (233 mL of 1 M dichloromethane solution) for 1 h, and then reacted for 0.5 h. Post-treatment: absolute methanol (700 mL) was added, and the mixture was stirred for ten minutes and then added with sodium bicarbonate solution to adjust pH to alkaline. Liquid separation was performed, and the aqueous phase was extracted with dichloromethane (500 mL×2), dried, filtered, and concentrated. The residue was dissolved in absolute methanol (350 mL), and the mixture was stirred for ten minutes and filtered. The solid was washed with a small amount of methanol (more than 80% of TrOMe was removed at this step), and the filtrate was concentrated. The residue was washed twice with toluene to remove the residual methanol, thus obtaining the final product (about 190 g).

The crude product 5 from the previous step was dissolved in dichloromethane (1500 mL), and camphorsulfonic acid (racemate, 16 g) was added. The mixture was cooled down in a water bath, added dropwise slowly with PMB trichloroimidate (158 g), warmed to room temperature and then reacted overnight. Post-treatment: Saturated sodium bicarbonate solution was added and liquid separation was performed. The aqueous phase was extracted with dichloromethane, and the organic phase was filtered to remove the solid camphorsulfonate, washed with saturated sodium chloride, dried, filtered, and concentrated to give a crude product of Compound 6 (about 313 g).

The crude product of Compound 6 obtained in the previous step was dissolved in tetrahydrofuran (700 mL), and then the mixture was cooled down in an ice bath, added dropwise slowly with borane dimethyl sulfide (10 M, 70 mL) under argon atmosphere, warmed to room temperature, reacted for ten minutes, and then heated to 55-60° C. and reacted overnight. Post-treatment: the mixture was cooled down in an ice bath, added dropwise slowly with methanol to quench the reaction (until no bubbles were generated), and concentrated under reduced pressure. The residue was dissolved in ethyl acetate, washing with saturated sodium bicarbonate, extracted with ethyl acetate, dried and concentrated. Methanol was added to the residue and then evaporated off, and this procedure was repeated twice. Column chromatography was performed to give Compound 7 (about 156 g, total yield: 68%). $^1$H NMR (500 MHz, CDCl$_3$) δ 7.72 (t, J=6.7 Hz, 4H), 7.57-7.48 (m, 2H), 7.43 (t, J=7.5 Hz, 4H), 7.22 (d, J=8.2 Hz, 2H), 6.91 (d, J=8.2 Hz, 2H), 4.50-4.34 (m, 2H), 3.96 (dt, J=7.8, 4.5 Hz, 2H), 3.87 (s, 3H), 3.79 (td, J=7.1, 3.5 Hz, 1H), 3.55 (td, J=8.5, 7.3, 4.1 Hz, 2H), 3.43 (dd, J=9.7, 6.7 Hz, 1H), 1.83 (ddt, J=11.3, 7.8, 3.9 Hz, 1H), 1.76 (q, J=12.7, 1H), 1.10 (s, 9H).

1.3. Synthesis of Compound 9

Compound 7 (103.4 g) was dissolved in acetonitrile (1 L), and then SM2 (4.7 g), potassium carbonate (37.5 g), potassium iodide (38.2 g) and benzyl bromide (37.3 mL) were added. The mixture was heated to 70-80° C. and reacted for 3-5 h (the disappearance of starting materials or the remaining of a few starting materials with no more change as detected by a dot plate). Post-treatment: The mixture was added with water, extracted with ethyl acetate for 2-3 times, dried and concentrated, and the product was directly used in the next step.

The crude product of Compound 8 was dissolved in tetrahydrofuran (314 mL), and tetrabutylammonium fluoride (TBAF, 314 mL) was added, and the mixture was reacted overnight at 25° C. Post-treatment: The mixture was concentrated under reduced pressure, and the residue was dissolved in water and ethyl acetate. Liquid separation was performed and ethyl acetate was added for extraction. Drying, concentration, and column chromatography (petroleum ether:ethyl acetate=2:1-1:1) were performed to give Compound 9 (about 62 g, total yield over two steps: about 86%). $^1$H NMR (400 MHz, CDCl$_3$) δ 7.44-7.21 (m, 7H), 6.85 (s, 2H), 4.50 (s, 2H), 4.47 (s, 2H), 3.82 (m, 1H), 3.79 (s, 3H), 3.76-3.64 (m, 3H), 3.65-3.54 (m, 2H), 1.89 (m, 1H), 1.85-1.72 (m, 1H).

Example 2. Synthesis of Compound 10

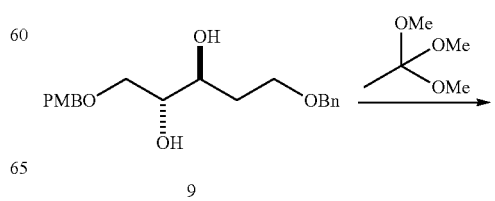

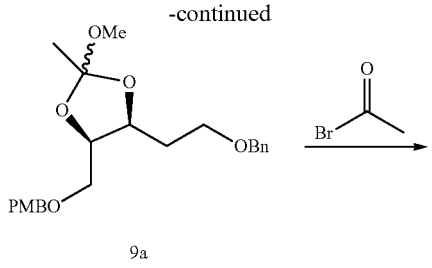

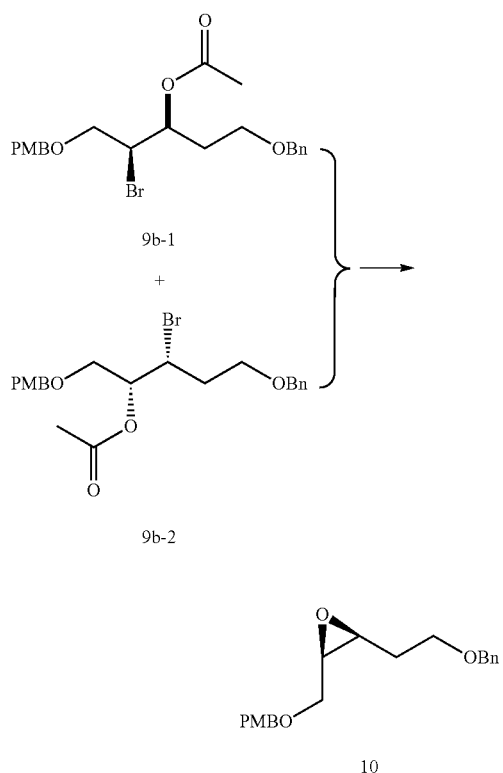

Compound 9 (149.5 g) was dissolved in DCM (818 mL), PPTs (5.4 g) was added, and trimethyl orthoacetate (82.4 mL) was added dropwise. Then the mixture was reacted at room temperature for 1 h, and the solvent was evaporated off to give a mixture 9a of product and epimer. The Compound 9a obtained above is redissolved in DCM (818 mL), and acetyl bromide (47.9 mL) was added dropwise. Then the resulting mixture was reacted for 0.5 h at room temperature, and the solvent was evaporated off to give a mixture of compounds 9b-1 and 9b-2. The mixture of the compounds 9b-1 and 9b-2 was dissolved in absolute methanol (1500 mL), and potassium carbonate (119 g) was added, and the resulting mixture was reacted at room temperature for 8 h. Post-treatment: The resulting mixture was added with saturated ammonium chloride solution, extracted with DCM, dried, filtered, concentrated, and subjected to silica gel column chromatography to give a refined product of Compound 10 (123 g, yield: 87%). $^1$H NMR (400 MHz, CDCl$_3$) δ 7.38-7.25 (m, 7H), 6.87 (d, J=13.2 Hz, 2H), 4.60-4.38 (m, 4H), 3.79 (s, 3H), 3.73-3.65 (m, 1H), 3.62 (d, J=11.5 Hz, 2H), 3.56-3.44 (m, 1H), 3.25-3.17 (m, 1H), 3.13 (s, 1H), 2.00-1.66 (m, 2H).

Example 3. Synthesis of Compound 11

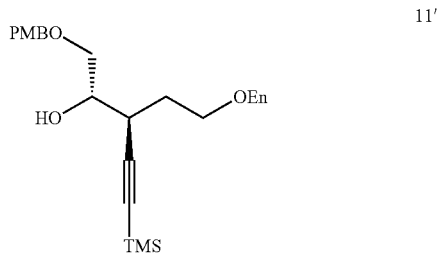

Under argon atmosphere, trimethylsilyl acetylene (15.5 g) was dissolved in anhydrous toluene (300 mL), and the mixture was cooled to −50° C., added dropwise slowly with a solution of 2.5 M n-BuLi in n-hexane (64 mL), and then stirred and reacted for 30 min. A solution of Compound 10 in toluene (dissolving 26 g of Compound 10 in 100 mL of toluene) was added dropwise and then BF$_3$Et$_2$O (22.6 g) was added dropwise slowly while maintaining the temperature not higher than −30° C. Then the resulting mixture was reacted for 3 h. After the reaction was completed as detected by TLC, the mixture was treated with saturated ammonium chloride (300 mL). The liquid separation was performed, and the aqueous phase was extracted twice with ethyl acetate (200 mL×2). The organic phases were combined, washed with saturated sodium chloride (300 mL×2), dried over anhydrous sodium sulfate, filtered off the drying agent, and concentrated to give a crude product (44 g), which was separated by silica gel column chromatography. The results of column chromatography were as follows: 22 g of Compound 11 was obtained (yield: 65%), and 10 g of the regioisomer shown as the following formula 11' was present.

Compound 11 $^1$H NMR (500 MHz, CDCl$_3$) δ 7.38-7.15 (m, 7H), 6.87 (d, J=6.8 Hz, 2H), 4.56-4.45 (m, 4H), 4.00 (tt, J=6.3, 3.2 Hz, 1H), 3.80 (d, J=2.3 Hz, 3H), 3.75-3.57 (m, 4H), 2.81 (tt, J=5.0, 2.8 Hz, 1H), 2.61 (d, J=6.5 Hz, 1H), 1.95 (h, J=6.5 Hz, 1H), 1.89-1.80 (m, 1H), 0.15 (d, J=2.4 Hz, 9H). HPLC showed the content of 11' in Compound 11 was ≤0.1%, and the content of other epimers in Compound 11 was ≤0.1%.

Example 4. Synthesis of Compound 16

4.1. Synthesis of Compound 13

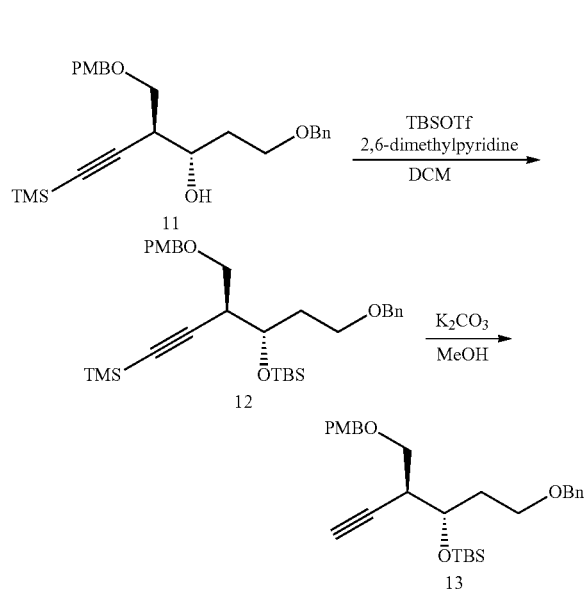

In an ice-water bath, Compound 11 (21 g) was dissolved in anhydrous dichloromethane (160 mL), and 2,6-dimethylpyridine (6.8 g) and tert-butyldimethylsilyl trifluoromethanesulfonate (TBSOTf, 15.6 g) were added dropwise successively. Then the mixture was warmed to room temperature and reacted for 1 h. After the reaction was completed as detected by TLC, the mixture was added with saturated aqueous ammonium chloride solution (200 mL) to quench the reaction, and then the liquid separation was performed. The aqueous phase was extracted with dichloromethane (200 mL×2), and the organic phases were combined, washed with 1 N hydrochloric acid to remove the 2,6-dimethylpyridine, then washed with saturated sodium chloride (200 mL×2), dried over anhydrous sodium sulfate and filtered. The filtrate was concentrated to give a crude product (Compound 12, 25.7 g) in the form of a brown yellow oil. The crude product of Compound 12 was dissolved in absolute methanol (200 mL), and potassium carbonate powder (13.5 g) was added. The mixture was reacted overnight at room temperature. After the reaction was completed as detected by TLC, ethyl acetate (200 mL) was added to dilute the reaction solution and the solid was filtered off through celite. The solid was washed with ethyl acetate until no product was remained, and the filtrate was concentrated to give a brown yellow viscous substance. Ethyl acetate (200 mL) was added, and the mixture was sufficiently stirred for dissolving and filtered through celite. The filter cake was washed with ethyl acetate until no product was remained, and the filtrate was concentrated to give a crude product (30 g) in the form of a brown yellow oil, which was separated by silica gel column chromatography to give Compound 13 (about 20.7 g, yield over two steps: 90%) in the form of a colorless oil. Compound 13 $^1$H NMR (400 MHz, CDCl$_3$) δ 7.30-7.22 (m, 3H), 7.24-7.13 (m, 4H), 6.85-6.72 (m, 2H), 4.77 (s, 1H), 4.50-4.24 (m, 4H), 4.13-3.80 (m, 1H), 3.64-3.39 (m, 3H), 2.84-2.65 (m, 1H), 2.07-1.97 (m, 1H), 1.90 (dt, J=12.7, 6.1 Hz, 1H), 1.72 (dd, J=13.8, 7.0 Hz, 1H), 0.81 (s, 9H), −0.01 (s, 6H).

4.2. Synthesis of Compound 15

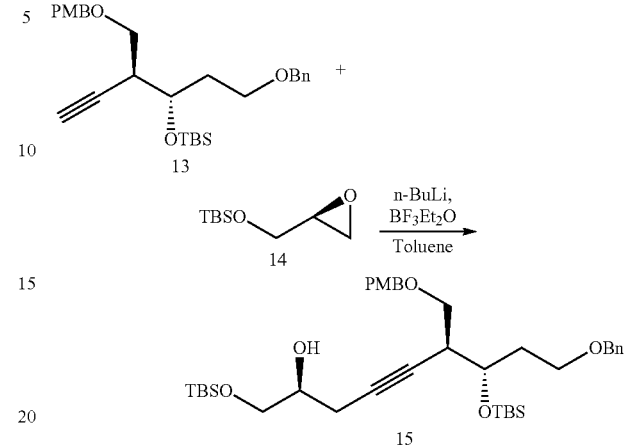

Under argon atmosphere, Compound 13 (10.8 g) was dissolved in anhydrous toluene (100 mL), and the mixture was cooled to −78° C., added dropwise with a solution of 2.5 N n-butyllithium in n-hexane (11 mL), and reacted for 30 min. Compound 14 (5.64 g, a commercially available product, with an optical purity of >99%) was dissolved in toluene (50 mL), and the solution was then added to the reaction system. Then BF$_3$Et$_2$O (4.0 g) was added dropwise slowly. The resulting mixture was reacted for 2 h while maintaining the temperature unchanged. After the reaction was completed as detected by TLC, the mixture was added with saturated ammonium chloride (150 mL) to quench the reaction, and then the liquid separation was performed. The aqueous phase was extracted with ethyl acetate (150 mL×2), and the organic phases were combined, washed with saturated sodium chloride (150 mL×2), dried over anhydrous sodium sulfate and filtered. The filtrate was concentrated to give a crude product (17.8 g) in the form of oil, which was separated by silica gel column chromatography to give Compound 15 (about 14.5 g, yield: 96%). Compound 15 $^1$H NMR (500 MHz, CDCl$_3$) δ 7.42-7.24 (m, 7H), 6.90 (d, J=8.0 Hz, 2H), 4.60-4.40 (m, 4H), 4.07 (d, J=7.3 Hz, 1H), 3.90-3.74 (m, 5H), 3.75-3.59 (m, 2H), 3.53 (q, J=6.1, 5.1 Hz, 3H), 2.79 (d, J=6.8 Hz, 1H), 2.45 (d, J=6.0 Hz, 1H), 2.13-1.97 (m, 1H), 1.88-1.71 (m, 2H), 1.42-1.22 (m, 2H), 1.02-0.84 (m, 18H), 0.10 (s, 6H), 0.07 (s, 6H).

4.3. Synthesis of Compound 16

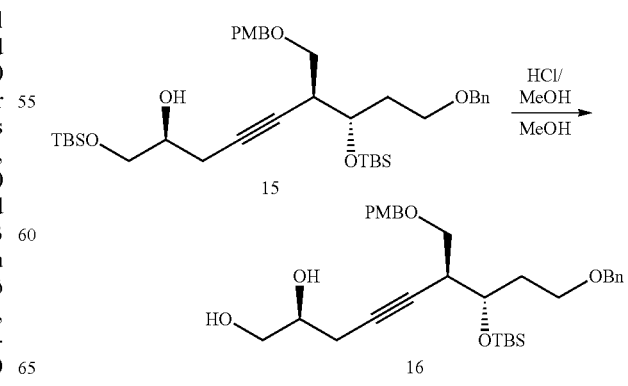

Under room temperature, Compound 15 (46 g) was dissolved in absolute methanol (500 mL) at room temperature and 3 N HCl/MeOH solution (13 mL) was added, and the mixture was reacted overnight at room temperature. After the reaction was completed as detected by TLC, aqueous ammonia (8 mL, 25-28%) was added, and the mixture was stirred to quench the reaction, dried over anhydrous sodium sulfate to remove water, and filtered. The residue was washed with ethyl acetate, and the filtrate was concentrated to give a light yellow oil substance (34.2 g), which was recrystallized with ethyl acetate/n-hexane to give a white crystal (26 g), a single product as detected by TLC. The white crystal was recrystallized again to give Compound 16 (25.2 g, yield: 83.3%, optical purity: >99.9%) in the form of a white crystal, and HPLC pattern is shown in FIG. 1. Compound 16 $^1$H NMR (500 MHz, methanol-$d_4$) δ 7.35-7.24 (m, 7H), 6.90 (dd, J=8.6, 2.9 Hz, 2H), 4.66-4.32 (m, 4H), 3.99 (dd, J=8.1, 4.3 Hz, 1H), 3.80 (s, 3H), 3.74-3.34 (m, 7H), 2.74 (s, 1H), 2.56-2.24 (m, 2H), 1.91 (td, J=7.9, 6.9, 3.1 Hz, 2H).

Example 5. Synthesis of Compound 20

5.1. Synthesis of Compound 17

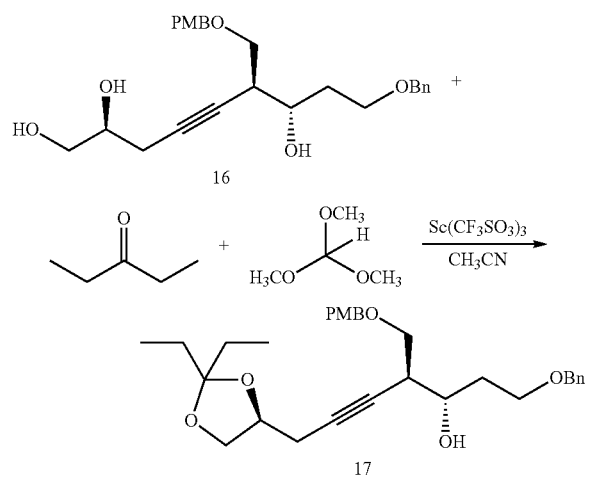

Compound 16 (24.2 g) was dissolved in acetonitrile (70 mL), and then pentanone (25 mL), trimethyl orthoformate (9.8 mL) and scandium trifluoromethanesulfonate (270 mg) were added successively. The mixture was reacted at room temperature for 1 h. After the reaction was completed as detected by TLC, the reaction solution was added with triethylamine to quench the reaction, and evaporated off the solvent to give a crude product (29.4 g), which was separated by column chromatography to give Compound 17 (26.6 g, yield: 95%). $^1$H NMR (500 MHz, CDCl$_3$) δ 7.50-7.08 (m, 7H), 6.87 (d, J=8.2 Hz, 2H), 4.60-4.33 (m, 4H), 4.19 (t, J=6.4 Hz, 1H), 4.08 (t, J=7.1 Hz, 1H), 4.04-3.92 (m, 1H), 3.80 (s, 3H), 3.76-3.43 (m, 5H), 2.87-2.64 (m, 2H), 2.56 (dd, J=16.4, 4.7 Hz, 1H), 2.42 (dd, J=16.5, 7.6 Hz, 1H), 1.93 (dd, 0.1=14.9, 7.9 Hz, 1H), 1.79 (dq, J=9.6, 4.7 Hz, 1H), 1.63 (dq, J=22.5, 7.9, 7.4 Hz, 4H), 0.89 (q, J=7.0 Hz, 6H)

5.2. Synthesis of Compound 18

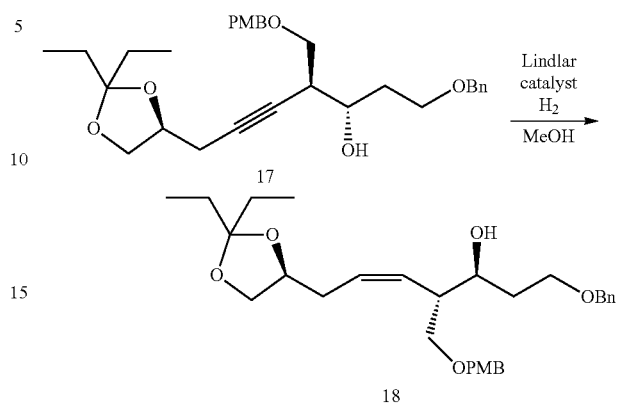

Compound 17 (23.8 g) was dissolved in absolute methanol (150 mL), and a Lindlar catalyst (2.4 g) was added. Hydrogenation reaction under normal pressure was carried out, and the reaction progress was monitored by TLC until the starting materials disappeared completely. The catalyst was filtered out, and the filtrate was concentrated to give a crude product of Compound 18 (23.6 g), which was directly used in the next step without further purification. $^1$H NMR (500 MHz, CDCl$_3$) δ 7.35-7.23 (m, 7H), 6.86 (d, J=8.2 Hz, 2H), 5.61-5.55 (m, 2H), 4.51 (s, 2H), 4.44 (t, 0.1=12.3 Hz, 2H), 4.10-4.05 (m, 1H), 4.03-3.99 (m, 2H), 3.80 (s, 3H), 3.70-3.61 (m, 2H), 3.57 (t, J=8.0 Hz, 1H), 3.49-3.43 (m, 2H), 3.06 (s, 1H), 2.70 (s, 1H), 2.40 (dt, J=12.6, 5.7 Hz, 1H), 2.27 (dt, J=14.1, 5.9 Hz, 1H), 1.83-1.74 (m, 1H), 1.62 (dt, J=15.6, 7.9 Hz, 4H), 0.89 (q, J=7.7 Hz, 6H).

5.3. Synthesis of Compound 19

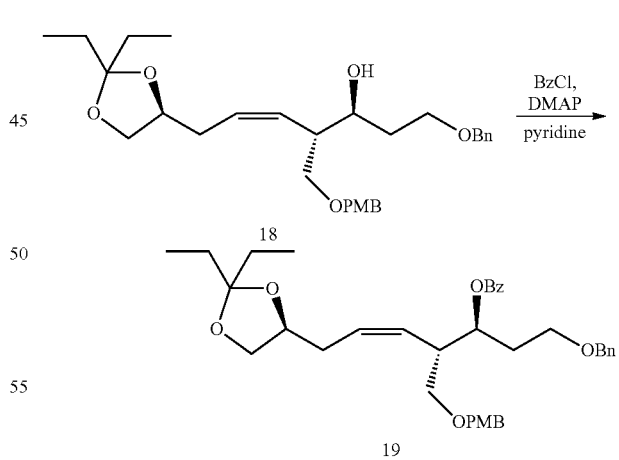

In an ice-water bath, Compound 18 (8.3 g) was dissolved in pyridine (50 mL), and benzoyl chloride (BzCl, 2.58 g) was added slowly and DMAP (200 mg) was added. The mixture was warmed to room temperature and reacted for 3 h. After the reaction was completed as detected by TLC, the reaction solution was diluted with ethyl acetate (100 mL) and added with water (100 mL) to quench the reaction. The liquid separation was performed. The aqueous phase was extracted with ethyl acetate (100 mL×2), and the organic phases were combined, washed with water (200 mL×2), then washed to neutral with 1 N diluted hydrochloric acid, washed with saturated sodium bicarbonate to remove residual HCl, finally washed with saturated sodium chloride, dried over anhydrous sodium sulfate, and filtered. The filtrate was concentrated to give a crude product (17 g), which was separated by column chromatography to give Compound 19 (about 10.1 g, yield: 99%). H NMR (400 MHz, CDCl₃) δ 8.02-7.95 (m, 2H), 7.58-7.54 (m, 1H), 7.44-7.41 (m, 2H), 7.28-7.26 (m, 5H), 7.20 (d, J=9.4 Hz, 2H), 6.78 (d, J=8.0 Hz, 2H), 5.68-5.56 (m, 3H), 4.43 (d, J=2.9 Hz, 3H), 4.36 (d, J=2.8 Hz, 2H), 4.09-4.02 (m, 1H), 3.97-3.93 (m, 1H), 3.75 (s, 3H), 3.53-3.50 (m, 2H), 3.49-3.42 (m, 2H), 3.33 (dd, J=9.3, 6.3 Hz, 1H), 3.03-2.97 (m, 1H), 2.44-2.28 (m, 2H), 2.07-1.99 (m, 2H), 1.96-1.88 (m, 1H), 1.66-1.57 (m, 4H), 0.89 (dd, J=14.7, 7.2 Hz, 6H).

5.4. Synthesis of Compound 20

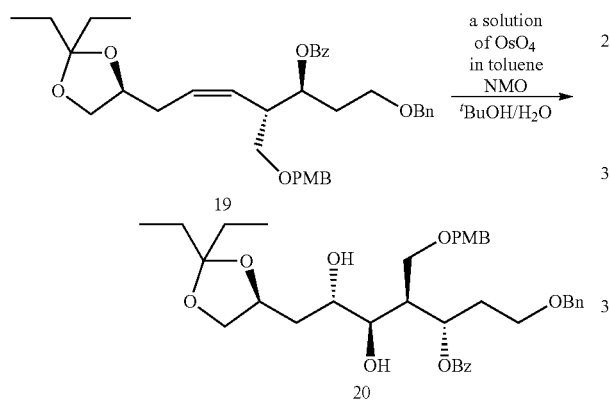

Under room temperature, Compound 19 (10 g) was dissolved in a mixed solvent of tert-butanol/water (20 mL/20 mL), and NMO (5.9 g) and a solution of osmium tetroxide in 0.05 M toluene solution (11 mL) were added successively. The mixture was heated to 45° C., stirred and reacted for 24 h. After the reaction was almost completed as detected by TLC, the mixture was added with saturated sodium sulfite (50 mL), stirred to quench the reaction, and extracted with ethyl acetate (100 mL×3). The organic phases were combined, washed with water (200 mL×2), washed with saturated sodium chloride (200 mL×2), dried over anhydrous sodium sulfate and filtered. The filtrate was concentrated to give a crude product (11 g), which was separated by silica gel column chromatography to give Compound 20 (about 9.8 g, yield: 92%). ¹H NMR (400 MHz, CDCl₃) δ 7.98 (dt, J=8.4, 1.6 Hz, 2H), 7.55 (tt, J=7.0, 1.3 Hz, 1H), 7.46-7.39 (m, 2H), 7.30-7.14 (m, 7H), 6.82 (dq, J=8.7, 2.2, 1.6 Hz, 2H), 5.51 (ddd, J=8.9, 7.4, 3.1 Hz, 1H), 4.51-4.35 (m, 4H), 4.35-4.24 (m, 1H), 4.04 (dd, J=8.0, 6.0 Hz, 1H), 3.89-3.64 (m, 7H), 3.62-3.51 (m, 2H), 3.47 (td, J=8.1, 5.0 Hz, 1H), 3.30 (t, J=5.5 Hz, 2H), 2.41 (tt, J=5.4, 2.3 Hz, 1H), 2.21 (dtd, J=14.5, 7.2, 3.2 Hz, 1H), 2.13-1.91 (m, 2H), 1.74 (ddd, J=14.2, 7.6, 4.5 Hz, 1H), 1.57 (dq, J=15.1, 7.5 Hz, 4H), 0.84 (dt, J=9.8, 7.5 Hz, 6H).

5.5. Synthesis of Compound 20

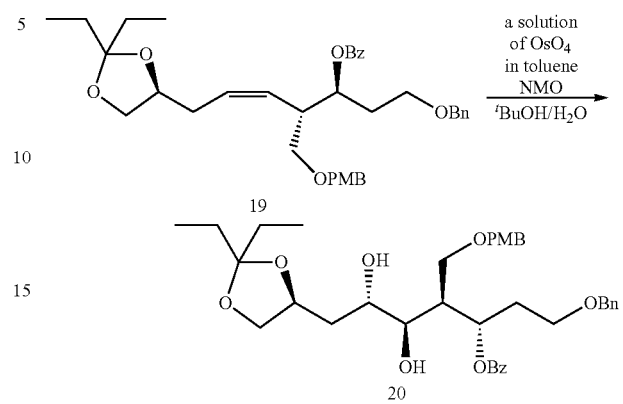

Under room temperature, Compound 19 (90 mg) was dissolved in a mixed solvent of tert-butanol/water (1 mL/1 mL), and DABCO (17 mg), NMO (53 mg) and a solution of osmium tetroxide in 0.05 M toluene solution (0.15 mL) were added successively. The mixture was then stirred and reacted for 24 h. After the reaction was almost completed as detected by TLC, the mixture was added with saturated sodium sulfite (5 mL), stirred to quench the reaction, and extracted with ethyl acetate (10 mL×3). The organic phases were combined, washed with water (10 mL×2), washed with saturated sodium chloride (10 mL×2), dried over anhydrous sodium sulfate and filtered. The filtrate was concentrated to give a crude product (110 mg), which was separated by silica gel column chromatography to give Compound 20 (67 mg, yield: 70%).

5.6. Synthesis of Compound 20-Ac

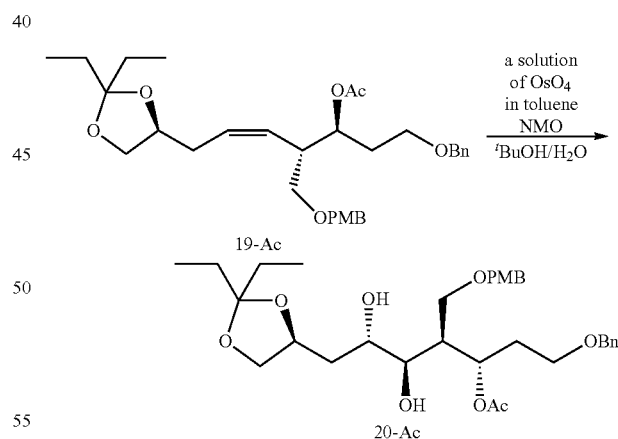

Under room temperature, Compound 19-Ac (55 g) was dissolved in a mixed solvent of tert-butanol/water (425 mL/425 mL). After being cooled to 0° C., the mixture was added successively with NMO (36 g) and a solution of osmium tetroxide in 0.05 M toluene (100 mL), heated to room temperature, stirred and reacted for 24 h. After part of starting materials were left as detected by TLC, the mixture was added with saturated sodium sulfite (500 mL) and stirred to quench the reaction, and extracted with ethyl acetate (500 mL/3). The organic phases were combined, washed with water (500 mL×2), washed with saturated sodium chloride (500 mL×2), dried over anhydrous sodium sulfate and filtered. The filtrate was concentrated to give a crude product (65 g), which was separated by silica gel column chromatography and the starting material Compound 19-Ac (14.8 g) was isolated to give Compound 20-Ac (about 38.2 g, yield: 89.6%, purity: 85%) (the main isomer therein is Compound 20-Ac'). $^1$H NMR (400 MHz, Chloroform-d) δ 7.35-7.27 (m, 5H), 7.21 (d, J=8.2 Hz, 2H), 6.86 (d, J=8.2 Hz, 2H), 5.32-5.20 (m, 1H), 4.48-4.40 (m, 4H), 4.34-4.30 (m, 1H), 4.10-4.05 (m, 1H), 3.80 (s, 31H), 3.73 (td, J=9.9, 4.7 Hz, 2H), 3.69-3.58 (m, 2H), 3.55-3.38 (m, 4H), 3.18 (s, 2H), 2.31-2.20 (m, 1H), 2.08-2.00 (m, 1H), 1.98 (s, 3H), 1.90-1.82 (m, 1H), 1.78-1.72 (m, 1H), 1.67-1.60 (m, 5H), 0.90 (t, J=7.4 Hz, 6H).

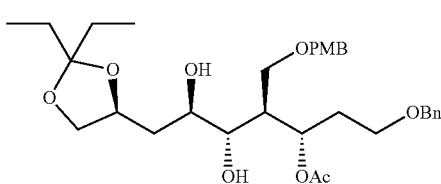

20-Ac'

Example 6. Synthesis of Compound 23

6.1. Synthesis of Compound 22

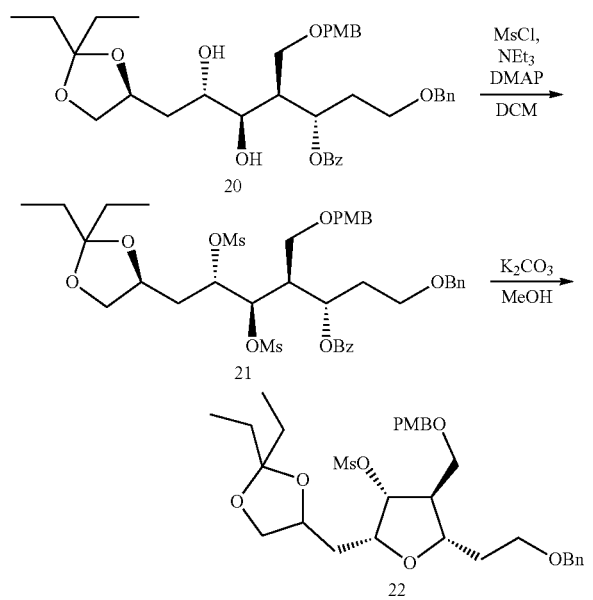

In an ice-water bath, Compound 20 (32 g) was dissolved in anhydrous dichloromethane (160 mL), and triethylamine (36.5 mL) and DMAP (640 mg) were added, followed by dropwise addition of MsCl (19.5 mL). Then the mixture was warmed to room temperature and reacted for 1 h. After the reaction was completed as detected by TLC, the mixture was added with saturated ammonium chloride (200 mL) to quench the reaction, and the liquid separation was performed. The aqueous phase was extracted with dichloromethane (200 mL×2), and the organic phases were combined, washed with water (250 mL×2), washed with saturated sodium chloride (250 mL×2), dried over anhydrous sodium sulfate, and concentrated to give a crude product of Compound 21 (about 39.4 g, theoretical yield: 39.8 g) in the form of a brown red oil, which was directly used in the next step without further purification. The crude product of Compound 21 (39.4 g) was dissolved in absolute methanol (300 mL), and anhydrous potassium carbonate powder (19 g) was added, and the mixture was stirred and reacted overnight. After the reaction was completed as detected by TLC, the mixture was concentrated under reduced pressure to evaporate off the solvent, added with water (300 mL) and extracted with dichloromethane (300 mL×2). The organic phases were combined, washed with saturated sodium chloride (300 mL×2), dried over anhydrous sodium sulfate and filtered. The filtrate was concentrated to give a crude product (33 g), which was separated by silica gel column chromatography to give Compound 22 (about 27 g, total yield over two steps: 90%). Compound 22 $^1$H NMR (500 MHz, CDCl$_3$) δ 7.38-7.17 ((m, 7H), 6.86 (d, J=8.0 Hz, 2H), 5.03 (s, 1H), 4.53-4.36 (m, 4H), 4.24 (h, J=6.5 Hz, 1H), 4.06 (t, J=6.9 Hz, 1H), 3.89 (q, 1=5.9, 5.5 Hz, 1H), 3.80 (s, 3H), 3.67 (q, J=6.6 Hz, 1H), 3.62-3.51 (m, 4H), 3.37 (t, J=8.6 Hz, 1H), 2.96 (s, 3H), 2.40 (q, J=6.6 Hz, 1H), 2.04 (dt, J=14.0, 6.8 Hz, 1H), 1.96 (dq, J=12.4, 6.3, 5.5 Hz, 3H), 1.62 (p, J=7.7 Hz, 4H), 0.89 (t, 1=7.5 Hz, 6H).

6.2. Synthesis of Compound 23

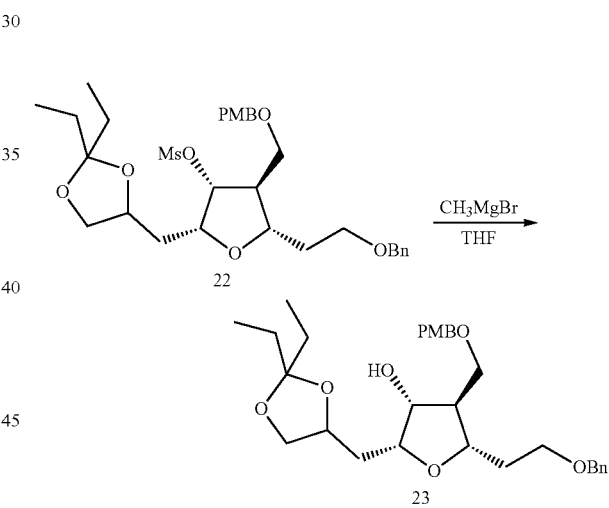

Figure 2:
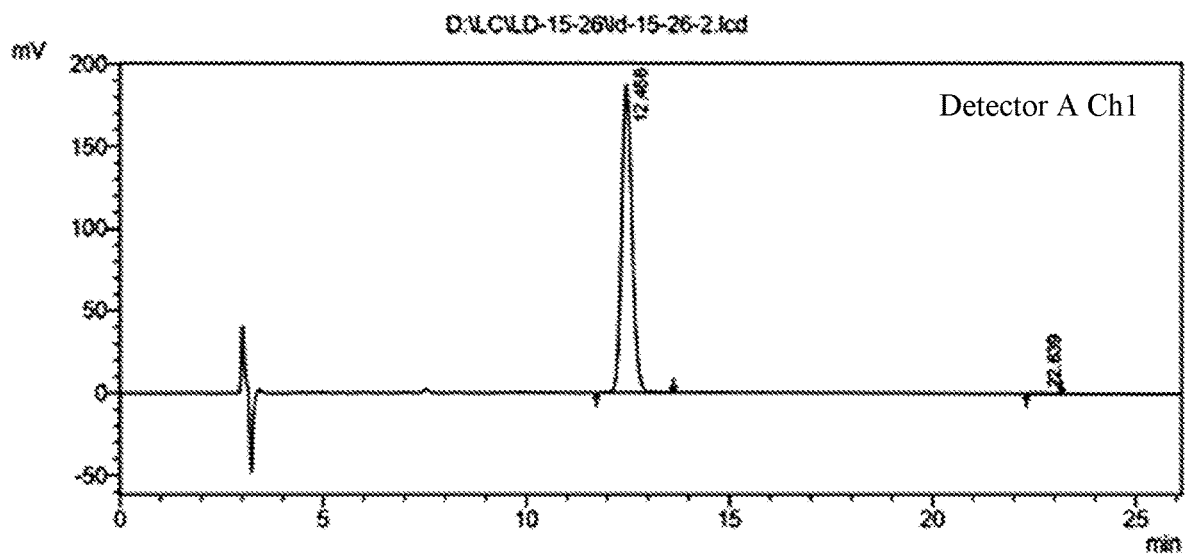
FIG. 2 is an HPLC pattern of Compound 23.

In an ice-water bath, Compound 22 (7.8 g) was dissolved in anhydrous tetrahydrofuran (80 mL), and a solution of 3 M methyl magnesium bromide in tetrahydrofuran (13.5 mL) was added dropwise. The mixture was warmed to room temperature and reacted overnight. After the reaction was completed as detected by TLC, the mixture was added dropwise with saturated ammonium chloride (100 mL) to quench the reaction and extracted with ethyl acetate (100 mL×3). The organic phases were combined, washed with saturated sodium chloride (200 mL×2), dried over anhydrous sodium sulfate and filtered. The filtrate was concentrated to give a crude product (8 g) in the form of a colorless oil, which was separated by silica gel column chromatography to give Compound 23 (5.8 g, yield: 86%) and Compound 23' (0.2 g). The purity of Compound 23 was >99.9%, and the HPLC pattern is shown in FIG. 2. The content of the impurity 23' shown as the following formula was 0.09%:

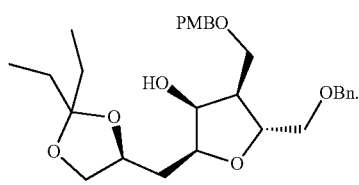

23'

¹H NMR (500 MHz, CDCl₃) δ 7.35-7.28 (m, 5H), 7.22 (d, J=8.1 Hz, 2H), 6.85 (d, J=8.0 Hz, 2H), 4.49 (s, 2H), 4.43 (s, 2H), 4.32-4.27 (m, 1H), 4.08-4.04 (m, 2H), 3.86 (q, J=5.9 Hz, 1H), 3.79 (s, 3H), 3.72-3.63 (m, 2H), 3.58 (dt, J=21.2, 7.5 Hz, 2H), 3.47 (d, J=6.3 Hz, 2H), 2.13 (dd, J=7.1, 3.9 Hz, 1H), 2.10-1.97 (m, 3H), 1.93 (dt, J=19.8, 6.3 Hz, 2H), 1.63 (dq, J=14.9, 7.4 Hz, 4H), 0.89 (q, J=7.3 Hz, 6H).

The examples of the present invention have been described above. However, the present invention is not limited to the above examples. Any modification, equivalent, improvement and the like made without departing from the spirit and principle of the present invention shall fall within the protection scope of the present invention.

The invention claimed is:

1. A compound having a structural formula of formula (XVI):

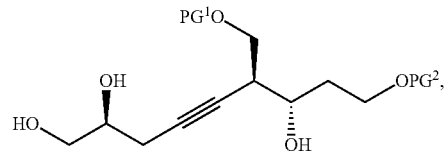

XVI wherein $PG^1$ and the $PG^2$ are the same or different, and are each independently selected from hydroxyl protecting groups except for silyl.

2. A preparation method of the compound of formula (XVI) according to claim 1, comprising: reacting a compound of formula (XV) under a condition where $PG^4$ and $PG^5$ are removed to give the compound of formula (XVI):

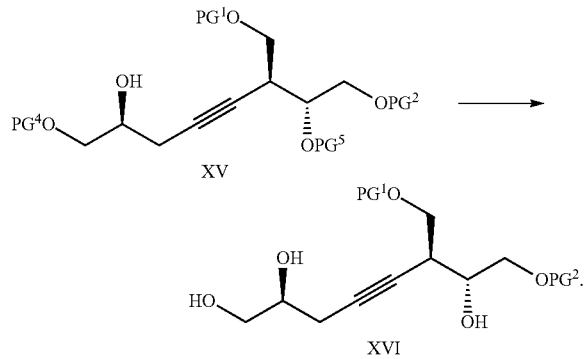

3. The preparation method of the compound of formula (XVI) according to claim 2, comprising:
the crude product of the compound of formula (XVI) is purified by recrystallization so that it contains a compound of formula (XVIa) shown below in an amount of ≤0.1%

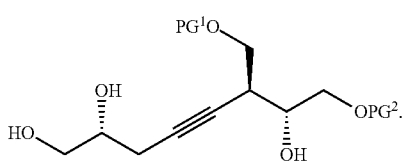

XVIa

4. The preparation method of the compound of formula (XVI) according to claim 2, comprising:
subjecting a compound of formula (XIII) and a compound of formula (XIV) to epoxide ring-opening to give the compound of formula (XV)

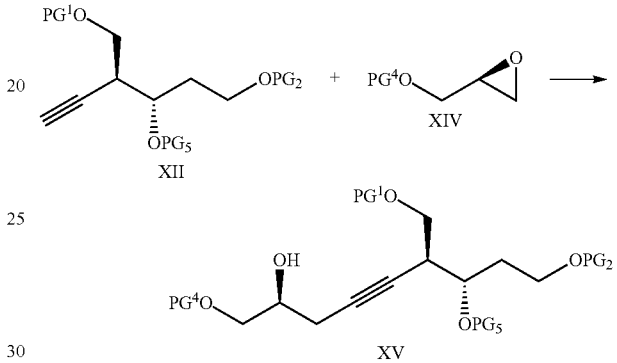

5. The preparation method of the compound of formula (XVI) according to claim 4, comprising:
hydroxyl protecting a compound of formula (XI) by reacting with a compound of formula $PG^5$-L to give the compound of formula (XIII),

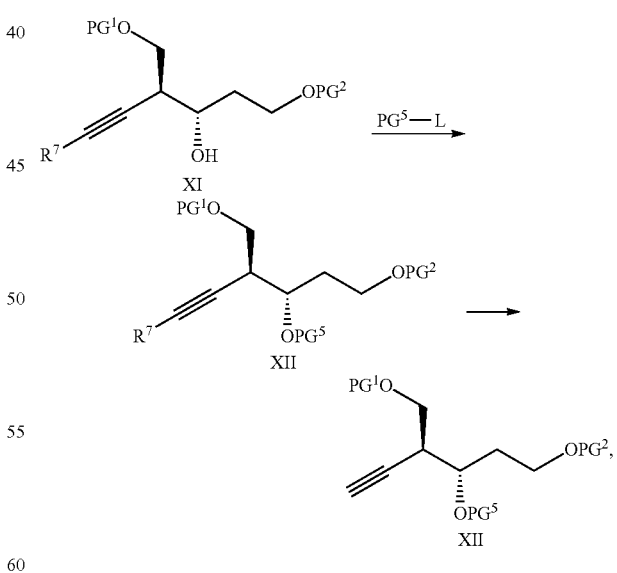

wherein, $R^7$ is hydrogen or a terminal alkyne protecting group.

6. The preparation method of the compound of formula (XVI) according to claim 5, comprising: reacting a compound of formula (X) with $R^7$—C≡CH in the presence of a strong base to give the compound of formula (XI)

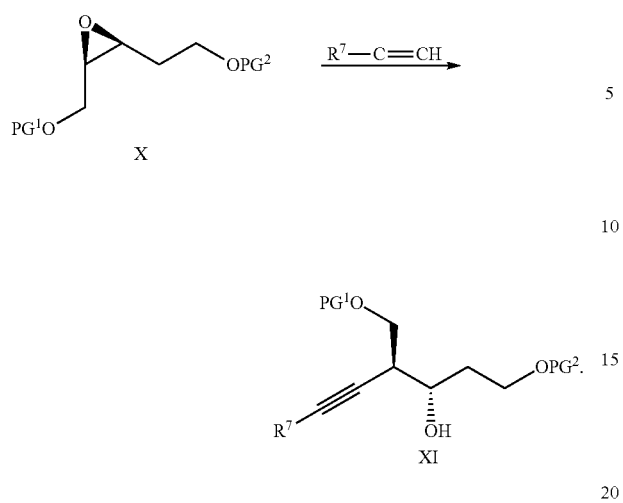

7. The preparation method of the compound of formula (XVI) according to claim 6, comprising:

(1) reacting a compound of formula (IX) with

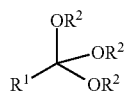

to give a compound of formula (IXa);

(2) reacting the compound of formula (IXa) with an acid halide

or a halosilane $R^3_3SiX$ to give a compound of formula (IXb-1) and/or a compound of formula (IXb-2); and (3) subjecting the compound of formula (IXb-1) and/or the compound of formula (IXb-2) to alcoholysis under basic conditions and further intramolecular $S_N2$ ring closing reaction to give the compound of formula (X);

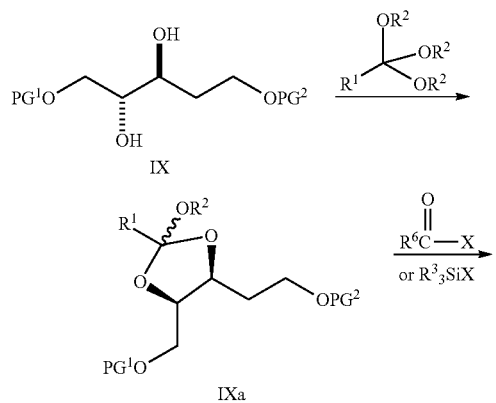

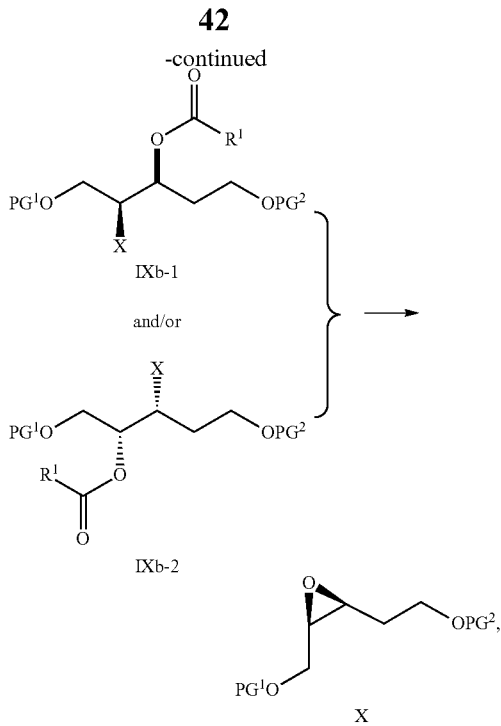

wherein, $R^1$, $R^2$ and $R^3$ are the same or different and are each independently selected from H, alkyl and aryl; $R^6$ is selected from alkyl; X is halogen.

8. A method for preparing a compound of formula (XIX), comprising:

reacting the compound of formula (XVI) of claim 1 with

and

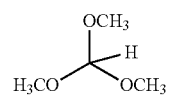

to obtain a compound of formula (XVII);

subjecting a compound of formula (XVII) to obtain a compound of formula (XVIII) is obtained;

reacting the compound of formula (XVIII) with $PG^6X$ to obtain the compound of formula (XIX), wherein $PG^6$ is independently selected from substituted or unsubstituted aromatic acyl, $PG^7$ is an o-dihydroxyl protecting group, and X is halogen,

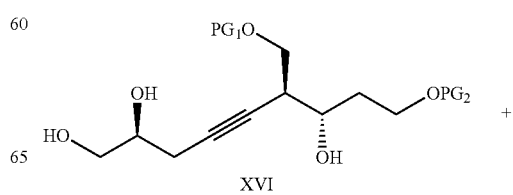

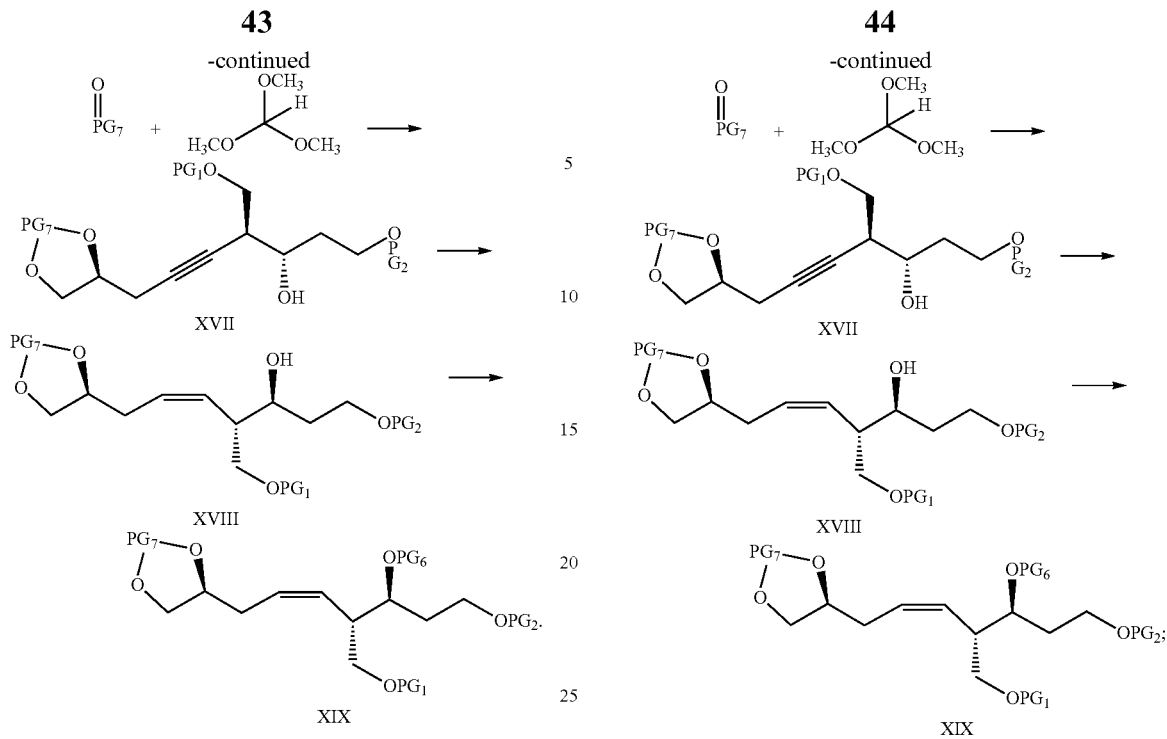

9. A method for preparing eribulin or a C27-C35 portion thereof, comprising:
reacting the compound of formula (XVI) of claim 1 with

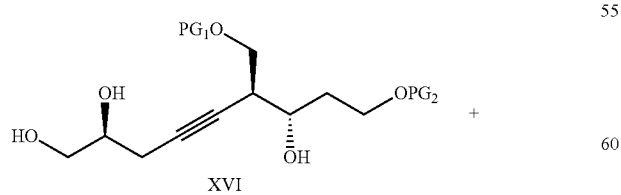

and $$\underset{H_3CO}{\overset{OCH_3}{\underset{|}{C}}}\underset{OCH_3}{\overset{H}{}}$$

to obtain a compound of formula (XVII);
subjecting the compound of formula (XVII) to hydrogenation reduction to obtain a compound of formula (XVIII);
reacting the compound of formula (XVIII) with $PG^6X$ to obtain the compound of formula (XIX), wherein $PG^6$ is independently selected from substituted or unsubstituted aromatic acyl, $PG^7$ is an o-dihydroxyl protecting group, and X is halogen, and subjecting the compound of formula (XIX) to dihydroxylation oxidation reaction in the presence of an oxidant to obtain the compound of formula (XX):

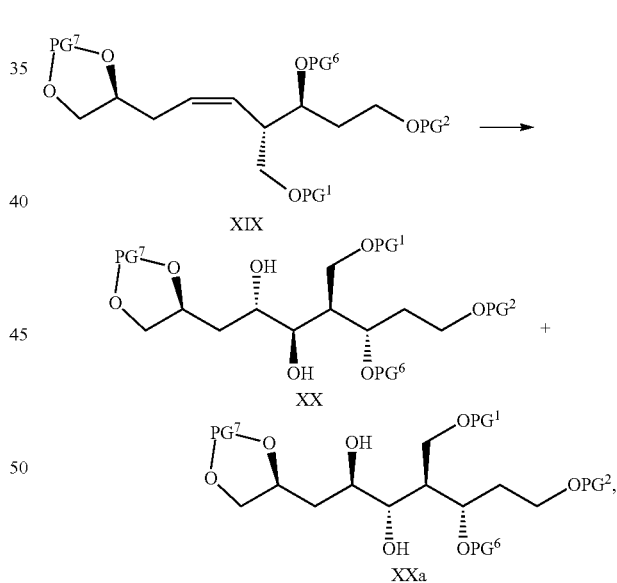

wherein $PG^1$ and $PG^2$ are the same or different, and are each independently selected from hydroxyl protecting groups except for silyl, $PG^6$ is selected from substituted or unsubstituted aromatic acyl, and $PG^7$ is an o-dihydroxyl protecting group.

* * * * *